United States Patent
Maekawa et al.

(10) Patent No.: US 12,247,223 B2
(45) Date of Patent: Mar. 11, 2025

(54) HUMAN LIVER-LIKE THREE-DIMENSIONAL STRUCTURE, METHOD FOR EVALUATING HEPATOTOXICITY AND HUMAN LIVER-LIKE COMPLEX

(71) Applicant: CYFUSE BIOMEDICAL K.K., Tokyo (JP)

(72) Inventors: Toshihiko Maekawa, Tokyo (JP); Eri Nagao, Tokyo (JP); Izumi Ide, Tokyo (JP); Sakura Kajiyama, Tokyo (JP)

(73) Assignee: CYFUSE BIOMEDICAL K.K., Tokyo (JP)

( * ) Notice: Subject to any disclaimer, the term of this patent is extended or adjusted under 35 U.S.C. 154(b) by 719 days.

(21) Appl. No.: 17/432,029

(22) PCT Filed: Feb. 21, 2020

(86) PCT No.: PCT/JP2020/007156
§ 371 (c)(1),
(2) Date: Aug. 18, 2021

(87) PCT Pub. No.: WO2020/171220
PCT Pub. Date: Aug. 27, 2020

(65) Prior Publication Data
US 2022/0315899 A1   Oct. 6, 2022

(30) Foreign Application Priority Data
Feb. 22, 2019 (JP) ................................ 2019-030240

(51) Int. Cl.
*C12N 5/071* (2010.01)
*C12Q 1/6883* (2018.01)
*G01N 33/50* (2006.01)

(52) U.S. Cl.
CPC ......... *C12N 5/0671* (2013.01); *C12Q 1/6883* (2013.01); *G01N 33/5014* (2013.01);
(Continued)

(58) Field of Classification Search
CPC .................................................... C12N 5/0671
See application file for complete search history.

(56) References Cited

U.S. PATENT DOCUMENTS

2006/0258692 A1   11/2006   Pines et al.
2017/0166870 A1   6/2017   Leite et al.
(Continued)

FOREIGN PATENT DOCUMENTS

JP     2006-504769 A      2/2006
WO   WO 2017/067970 A1   4/2017
(Continued)

OTHER PUBLICATIONS

English machine translation of Kizawa et al., WO 2017/200111 A1, 2017.*
(Continued)

*Primary Examiner* — Rosanne Kosson
(74) *Attorney, Agent, or Firm* — Birch, Stewart, Kolasch & Birch, LLP

(57) ABSTRACT

Long awaited is a human liver-like three-dimensional construct that makes it possible to carry out evaluation of human-specific toxicity and the like accurately and in a simple manner. The present invention provides a human liver-like three-dimensional construct comprising a heterospheroid, in which human hepatic cells and other human-derived cells which are not human hepatic cells are aggregated. This human liver-like three-dimensional construct is characterized in that the other human-derived cells are at least one selected from human hepatic stellate cells and the
(Continued)

Figure 1:
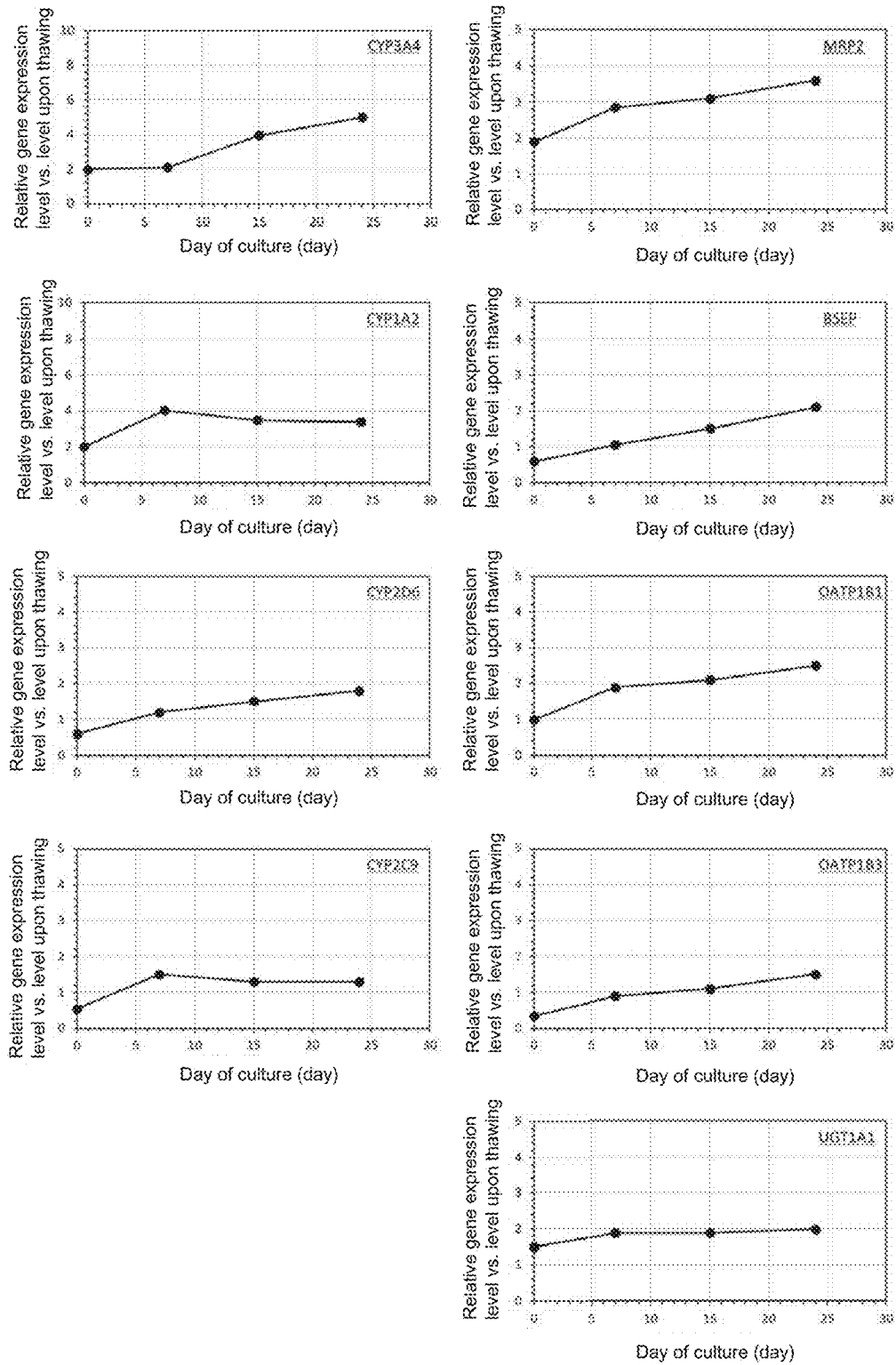

like, and the other human-derived cell to the human hepatic cell count ratio is at least 0.01 but less than 1.

20 Claims, 10 Drawing Sheets

Specification includes a Sequence Listing.

(52) U.S. Cl.
CPC ..... *G01N 33/5067* (2013.01); *C12N 2513/00* (2013.01); *C12Q 2600/178* (2013.01)

(56) References Cited

U.S. PATENT DOCUMENTS

| | | |
|---|---|---|
| 2019/0025288 A1 | 1/2019 | Boess et al. |
| 2019/0316093 A1 | 10/2019 | Messner et al. |

FOREIGN PATENT DOCUMENTS

| | | |
|---|---|---|
| WO | WO 2017/200111 A1 | 11/2017 |
| WO | WO 2018/115533 A1 | 6/2018 |

OTHER PUBLICATIONS

Japanese Office Action for Japanese Application No. 2021-502202, dated Dec. 5, 2023, with English translation.
Japanese Office Action for Japanese Application No. 2021-502202, dated May 21, 2024, with English translation.
"Construction of three-dimensional cellular structure using bio 3D Printer and hepatotoxicity assessment," Seminar presentation for experiencing 3D (spheroid) culture using iCell Hepatocytes 2.0, Cyfuse Biomedical K.K., Feb. 23, 2018, pp. 1-47, with English translation.
Costa De Freitas et al., "Modulation of miR-26a-5p and miR-15b-5p Exosomal Expression Associated with Clopidogrel-Induced Hepatotoxicity in HepG2 Cells," Frontiers in Pharmacology, vol. 8, 2017, 906/1-906/11 (11 pages total).
Ide, "Development of Drug Discovery Support Tool Using Bio 3D Printer," The 25th Annual Meeting of HAB Research Organization, Cyfuse Biomedicial K.K., May 25, 2018, pp. 1-50, with English translation.
Ide, "Development of Drug Discovery Support Tools Using Bio 3D Printer," The 25th Annual Meeting of HAB Research Organization, Cyfuse Biomedical K.K., May 25, 2018, 5 pages total, with English translation.
International Search Report for International Application No. PCT/JP2020/007156, dated May 26, 2020, with English translation.
Kajiyama et al., "Construction of a human liver model made using a bio-3D printer: Hepatotoxicity assessment of liver structures using fresh human hepatocytes (chimeric mouse-derived human hepatocytes)," The 45th Annual Meeting of the Japanese Society of Toxicology, Jul. 18, 2018, 2 pages total, with English translation.
Kajiyama et al., "Construction of bio 3D printed human livermodel: Toxicity evaluation of liver tissue using fresh human hepatocytes (derived from human hepatocyte chimeric mouse)," Cyfuse Biomedical K.K., WDB Co., Ltd., Program of the 45th Annual Meeting of the Japanese Society of Toxicology, P-17, Jun. 27, 2018. p. 217 (7 pages total), with English translation.
Kajiyama et al., "P-23 Construction of human liver model fabricated with bio 3D Printer: Toxicity assessment in liver structure using fresh human hepatocytes (human hepatocytes derived from chimeric mice)," Program of 1st Meeting of the Study Group on Mechanisms of Drug Toxicity, Cyfuse Biomedical K.K.. Jan. 5, 2019. p. 82 (3 pages total), with English translation.
Kajiyama et al., "Drug Discovery Support by Cyfuse Using 3D Structures," Bio Japan 2018, Oct. 10, 2018, 2 pages total, with English translation.
Kajiyama et al., "P-23 Construction of human liver structure fabricated using bio 3D printer: Toxicity assessments in liver structure using fresh human hepatocytes (human hepatocytes derived from chimeric mice)," 1st Meeting of the Study Group on Mechanisms of Drug Toxicity, Cyfuse Biomedical K.K., Jan. 10, 2019, pp. 1-4 (8 pages total), with English translation.
Khetani et al., "Microscale culture of human liver cells for drug development," Nature Biotechnology, vol. 26, No. 1, Jan. 2008, pp. 120-126.
Mosedale et al., "miR-122 Release in Exosomes Precedes Overt Tolvaptan-Induced Necrosis in a Primary Human Hepatocyte Micropatterned Coculture Model," Toxicological Sciences, vol. 161, No. 1, 2018, pp. 149-158.
Nagao et al., "Construction of a human liver model made using a bio-3D printer: Toxicity assessment comparison of structures and spheroids using human frozen primary hepatocytes," The 45th Annual Meeting of the Japanese Society of Toxicology, Jul. 18, 2018, 2 pages total, with English translation.
Nagao et al., "P-18 Construction of bio 3D printed human liver model: Comparison of hepatotoxicity assessment between spheroids and liver tissue using cryopreservedprimary human hepatocytes," Program of The 45th Annual Meeting of the Japanese Society of Toxicology, Cyfuse Biomedical K.K. WDB Co. Ltd. vol. 43 Supplement, Jun. 27, 2018, 6 pages total, with English translation.
Nagao et al., "Construction of human liver model fabricated with bio 3D printer: Comparison of toxicity assessment between structure and spheroids using cryopreserved primary human hepatocytes," Program of 1st Meeting of the Study Group on Mechanisms of Drug Toxicity, Cyfuse Biomedical K.K., Jan. 5, 2019, p. 81 (3 pages total) with English translation.
Nagao et al., "P-22 Construction of human liver model fabricated using bio 3D printer: Comparison of toxicity assessment between spheroids and structure using cryopreserved primary human hepatocytes," 1st Meeting of the Study Group on Mechanisms of Drug Toxicity, Cyfuse Biomedical K.K., Jan. 10, 2019, 12 pages total, with English translation.
Nagao et al., "The Future of Drug Discovery Research and Regenerative Medicine Envisioned by Bio 3D Printer," Journal of Pharmaceutical Science and Technology, Japan, vol. 78, No. 6, Nov. 1, 2018, pp. 275-278 (10 pages total), with English translation.
Nagao et al., Drug Discovery Support by Cyfuse Using 3D Structures, The 45th Annual Meeting of the Japanese Society of Toxicology, Jul. 18, 2018, 2 pages total, with English translation.
Nishito et al., "Tetrandrine, an anti-fibrotic substance, regulates autophagic pathway in hepatic stellate cells," Lecture abstracts of the 2014 Conference of Japan Society of Bioscience, Biotechnology, and Agrochemistry (online) DVD-R, Japan Society for Bioscience, Biotechnology, and Agrochemistry, 2014, 3 pages total, with English translation.
Ohkura et al., "Evaluation of Human Hepatocytes Cultured by Three-dimensional Spheroid Systems for Drug Metabolism," Drug Metab. Pharmacokinet., vol. 29, No. 5, 2014, pp. 373-378.
Shimizu, "Sho-saiko-to for protection against hepatic fibrosis and carcinoma," Journal of Clinical and Experimental Medicine, Oriental Medicine from Standpoint of Modern Western Medicine, 2003, 67-71, with English translation.

* cited by examiner

SEQUENCE LISTING

```
<160> NUMBER OF SEQ ID NOS: 8

<210> SEQ ID NO 1
<211> LENGTH: 22
<212> TYPE: RNA
<213> ORGANISM: Homo sapiens

<400> SEQUENCE: 1
uggaguguga caaugguguu ug                                                  22

<210> SEQ ID NO 2
<211> LENGTH: 22
<212> TYPE: RNA
<213> ORGANISM: Homo sapiens

<400> SEQUENCE: 2
aacgccauua ucacacuaaa ua                                                  22

<210> SEQ ID NO 3
<211> LENGTH: 21
<212> TYPE: RNA
<213> ORGANISM: Homo sapiens

<400> SEQUENCE: 3
cugaccuaug aauugacagc c                                                   21

<210> SEQ ID NO 4
<211> LENGTH: 22
<212> TYPE: RNA
<213> ORGANISM: Homo sapiens

<400> SEQUENCE: 4
cugccaauuc cauaggucac ag                                                  22

<210> SEQ ID NO 5
<211> LENGTH: 25
```

```
<212> TYPE: RNA
<213> ORGANISM: Homo sapiens

<400> SEQUENCE: 5
ucaagucacu agugguuccg uuuag                                         25

<210> SEQ ID NO 6
<211> LENGTH: 23
<212> TYPE: RNA
<213> ORGANISM: Homo sapiens

<400> SEQUENCE: 6
aaaauggugc ccuagugacu aca                                           23

<210> SEQ ID NO 7
<211> LENGTH: 22
<212> TYPE: RNA
<213> ORGANISM: Homo sapiens

<400> SEQUENCE: 7
acauacuucu uuauaugccc au                                            22

<210> SEQ ID NO 8
<211> LENGTH: 22
<212> TYPE: RNA
<213> ORGANISM: Homo sapiens

<400> SEQUENCE: 8
uggaauguaa agaaguaugu au                                            22
```

HUMAN LIVER-LIKE THREE-DIMENSIONAL STRUCTURE, METHOD FOR EVALUATING HEPATOTOXICITY AND HUMAN LIVER-LIKE COMPLEX

TECHNICAL FIELD

The present invention relates to a human liver-like three-dimensional construct comprising a heterospheroid, a method for assessing hepatotoxicity using said construct, and a human liver-like complex obtained by connecting two or more of said constructs.

BACKGROUND ART

For carrying out clinical tests requiring considerable money and time, there is a great need from the pharmaceutical companies for an in vitro human liver model for narrowing down drug discovery candidate compounds that are to be subjected to toxicity and metabolite tests. Human liver models that can be used for predicting toxicity in clinical tests are anticipated as a tool for enhancing efficiency and accelerating speed of drug discovery-related studies.

As one of the currently existing methods for producing an in vitro human liver model, a method comprising co-culturing hepatocytes and mouse fibroblasts for functional improvement is known (Non-patent documents 1 and 2).

A human liver model obtained by such a method, however, contains mouse-derived cells along with the human hepatocytes. Therefore, the effect of the metabolic system unique to mice need to be considered upon a drug toxicity test or a metabolite assessment. In doing so, a method that uses mouse-derived cells alone as a negative control has been employed. However, since the effect of the co-culture process on the mouse cells is not taken into consideration, it is hard to call them an accurate negative control and thus the effect of the mouse cells on the acquired drug assessment results cannot be completely eliminated.

Patent document 1 proposes a human liver-like three-dimensional construct fabricated using human hepatocytes and human-derived cells other than the human hepatocytes. The human liver-like three-dimensional construct of Patent document 1 can be used to accurately and simply assess human-specific toxicity and the like without considering the effect of the metabolic system unique to mice which has been a concern in a co-culture system using human hepatocytes and mouse fibroblasts, but there is still room for further improvement.

PRIOR ART DOCUMENTS

Patent Document

Patent document 1: International Patent Application Publication WO2017/200111

Non-patent Documents

Non-patent document 1: Khetani S. R. et al., Nat. Biotechnol. 26: 120-126 (2008)

Non-patent document 2: Ohkura T. et al., Drug Metab. Pharmacokinet. 29: 373-378 (2014)

SUMMARY OF INVENTION

Problem to be Solved by Invention

A human liver-like three-dimensional construct that enables accurate and simple assessment of human-specific toxicity and the like has been desired.

Means for Solving Problem

Thus, the present invention is as follows.

[1] A human liver-like three-dimensional construct comprising a heterospheroid formed of an aggregate of human hepatocytes and human-derived cells other than the human hepatocytes,
wherein the other human-derived cells are at least one kind selected from the group consisting of human hepatic stellate cells, human pulmonary fibroblasts, human aortic adventitial fibroblasts, human periodontal ligament fibroblasts, human intestinal myofibroblasts, human tenocytes, human astrocytes, human neonatal dermal fibroblasts, human synovial stromal cells, human brain capillary pericytes, human kidney mesangial cells, human cardiac fibroblasts, human aortic smooth muscle cells, human osteoblasts, normal human skeletal muscle cells, human dental pulp stem cells, human nucleus pulposus cells, human annulus fibrosus cells, human ligament cells, human chondrocytes, human Kupffer cells, human sinusoidal endothelial cells, human biliary epithelial cells, human adult dermal fibroblasts, human bone marrow-derived mesenchymal stem cells and human adipose-derived mesenchymal stem cells; and
the ratio of the number of the other human-derived cells to the number of the human hepatocytes is 0.01 or higher but lower than 1.

[2] The human liver-like three-dimensional construct according to [1] above, wherein the heterospheroids are stacked or blended.

[3] The human liver-like three-dimensional construct according to either one of [1] and [2] above, wherein the human hepatocytes and the other human-derived cells are homogeneously distributed.

[4] The human liver-like three-dimensional construct according to [3] above, wherein the other human-derived cells comprise human hepatic stellate cells.

[5] The human liver-like three-dimensional construct according to [4] above, wherein a cluster of the human hepatic stellate cells has a maximum projected area (equivalent circular) diameter of 100 μm.

[6] The human liver-like three-dimensional construct according to any one of [1]-[5] above, wherein a projected area (equivalent circular) diameter of the heterospheroid is 300-1000 μm.

[7] The human liver-like three-dimensional construct according to [6] above, wherein a projected area (equivalent circular) diameter of the heterospheroid is 400-600 μm.

[8] The human liver-like three-dimensional construct according to any one of [1]-[7] above, which is substantially spherical and has a projected area (equivalent circular) diameter of at least 1.0 mm.

[9] The human liver-like three-dimensional construct according to [8] above, which is substantially spherical and has a projected area (equivalent circular) diameter of 1.1-10.0 mm.

[10] The human liver-like three-dimensional construct according to [9] above, which is substantially spherical and has a projected area (equivalent circular) diameter of 1.2-5.0 mm.

[11] The human liver-like three-dimensional construct according to any one of [1]-[7] above, which has a hollow or solid substantially round or substantially polygonal cylindrical shape, where an average diameter of the cross sections thereof is 1.0-10.0 mm.

[12] The human liver-like three-dimensional construct according to any one of [1]-[7] above, which has a ring shape, where an average length of the minor axes at the bottom and at the top is 1.0-10.0 mm.

[13] The human liver-like three-dimensional construct according to any one of [1]-[7] above, which has a sheet shape with an average thickness of at least 300 μm.

[14] The human liver-like three-dimensional construct according to [13] above, which has a sheet shape with an average thickness of at least 500 μm.

[15] A method for assessing hepatotoxicity of a test substance to a human, the method comprising:
(1) a contact step in which the test substance is brought into contact with the human liver-like three-dimensional construct according to any one of [1]-[14] above; and
(2) a determination step in which presence or a degree of damage to the human liver-like three-dimensional construct is determined.

[16] The method according to [15] above, wherein the determination step comprises an exosome collection step in which exosomes released from the three-dimensional construct are collected, and a miRNA analysis step in which a miRNA contained in the exosomes is analyzed.

[17] The hepatotoxicity assessment method according to either one of [15] and [16] above, wherein the miRNA analysis step is carried out by a microarray or PCR technique.

[18] A human liver-like complex obtained by connecting two or more of the human liver-like three-dimensional constructs according to any one of [1]-[14] above.

[19] The human liver-like three-dimensional construct according to any one of [1]-[14] above, which is obtained by fusing two or more of the heterospheroids.

[20] The human liver-like three-dimensional construct according to any one of [4]-[14] above, wherein the other human cells comprise human hepatic stellate cells, and said human hepatic stellate cells are in a quiescent state.

[21] A method for assessing hepatotoxicity of a test substance to a human, comprising:
(1) a contact step in which the test substance is brought into contact with the human liver-like three-dimensional construct according to [20] above; and
(2) a determination step in which presence or a degree of damage to the human liver-like three-dimensional construct is determined.

[22] A method for producing a human liver-like three-dimensional construct, comprising the steps of:
mixing human hepatocytes and human-derived cells other than the human hepatocytes such that the ratio of the number of the other human-derived cells to the number of the human hepatocytes is 0.01 or higher but lower than 1, and culturing the mixture to obtain a heterospheroid formed of an aggregate of the human hepatocytes and the human-derived cells; and
blending or stacking the heterospheroids,
wherein the other human-derived cells are at least one kind selected from the group consisting of human hepatic stellate cells, human pulmonary fibroblasts, human aortic adventitial fibroblasts, human periodontal ligament fibroblasts, human intestinal myofibroblasts, human tenocytes, human astrocytes, human neonatal dermal fibroblasts, human synovial stromal cells, human brain capillary pericytes, human kidney mesangial cells, human cardiac fibroblasts, human aortic smooth muscle cells, human osteoblasts, normal human skeletal muscle cells, human dental pulp stem cells, human nucleus pulposus cells, human annulus fibrosus cells, human ligament cells, human chondrocytes, human Kupffer cells, human sinusoidal endothelial cells, human biliary epithelial cells, human adult dermal fibroblasts, human bone marrow-derived mesenchymal stem cells and human adipose-derived mesenchymal stem cells.

[23] A human liver-like three-dimensional construct obtained by the production method according to [22] above.

Effect of the Invention

The present invention provides a human liver-like three-dimensional construct that can exert functions similar to the liver functions in vivo, and a method for assessing hepatotoxicity of a test substance to a human using said human liver-like three-dimensional construct. In addition, the present invention also provides a human liver-like complex obtained by connecting a plurality of human liver-like three-dimensional constructs.

BREIF DESCRIPTION OF DRAWINGS

FIG. 1 Graphs showing results from gene expression analyses in the human liver-like three-dimensional construct A described in Experimental example 4.

Figure 2:
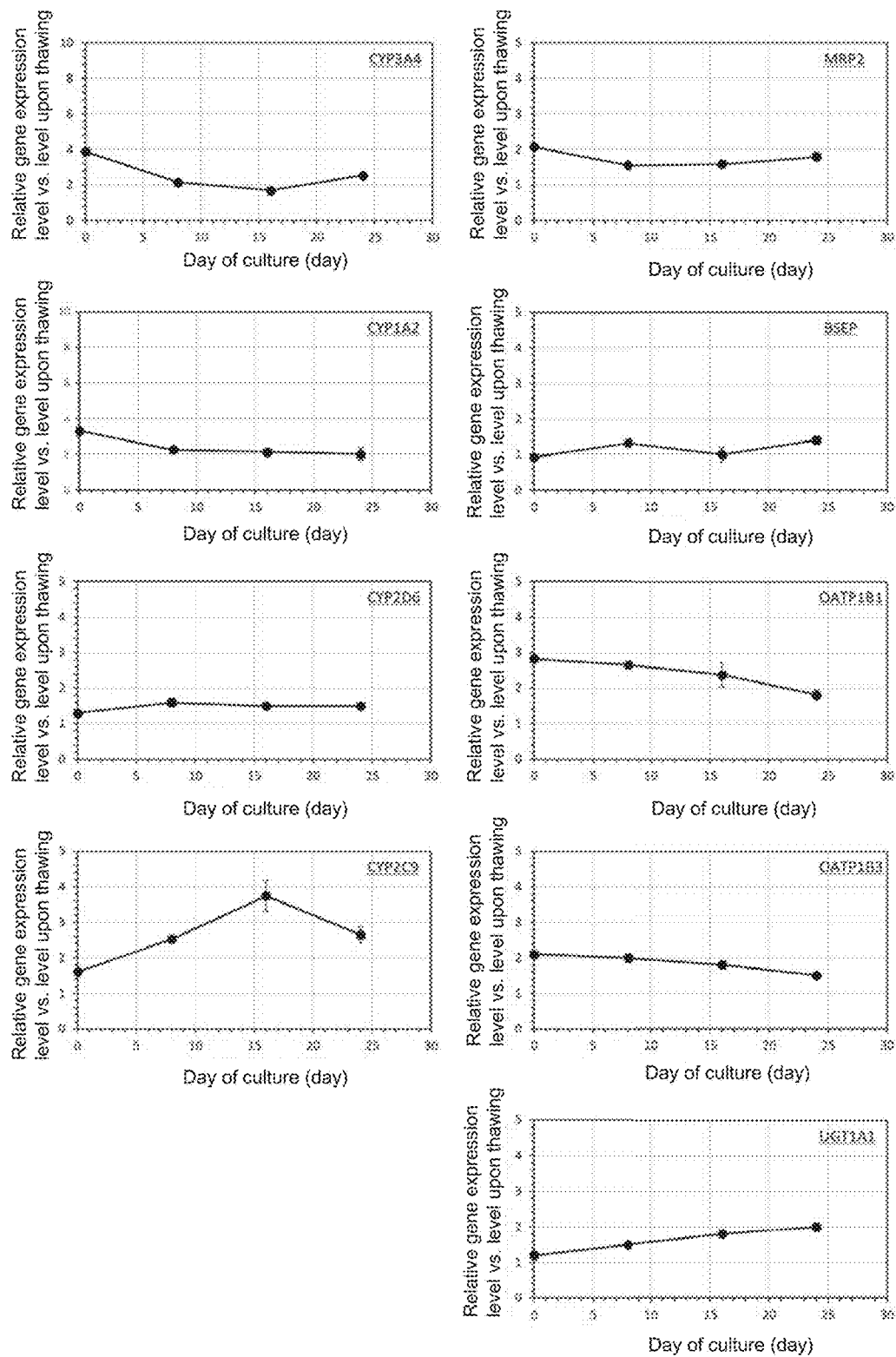

FIG. 2 Graphs showing results from gene expression analyses in the human liver-like three-dimensional construct B described in Experimental example 4.

Figure 3:
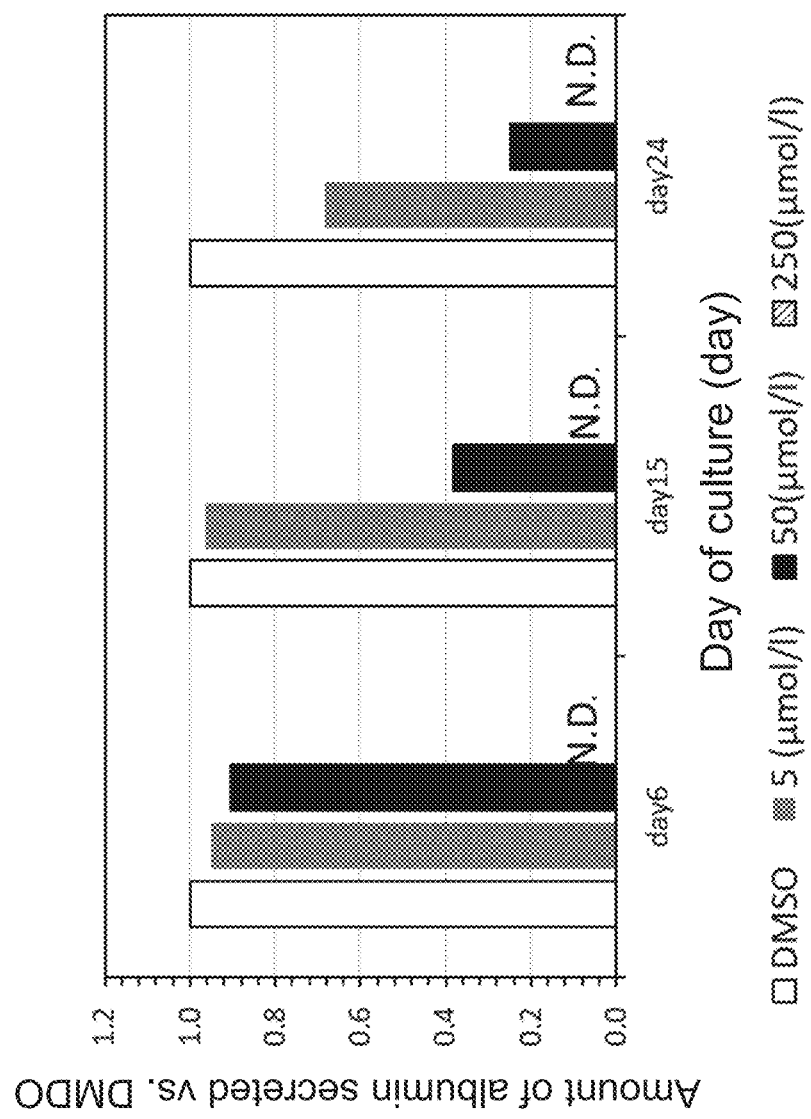

FIG. 3 A graph showing changes in the albumin concentrations in the media described in Experimental example 5.

Figure 4:
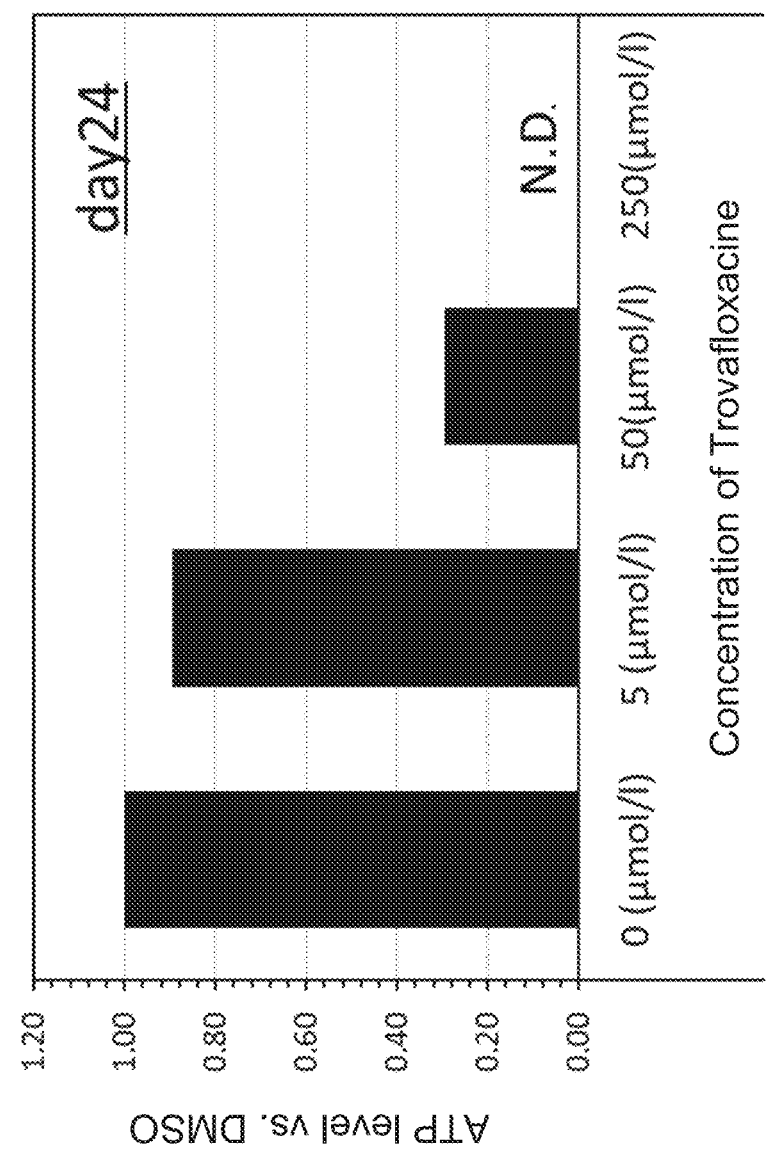

FIG. 4 A graph showing difference in the levels of ATP contained in the human liver-like three-dimensional constructs described in Experimental example 5.

Figure 5:
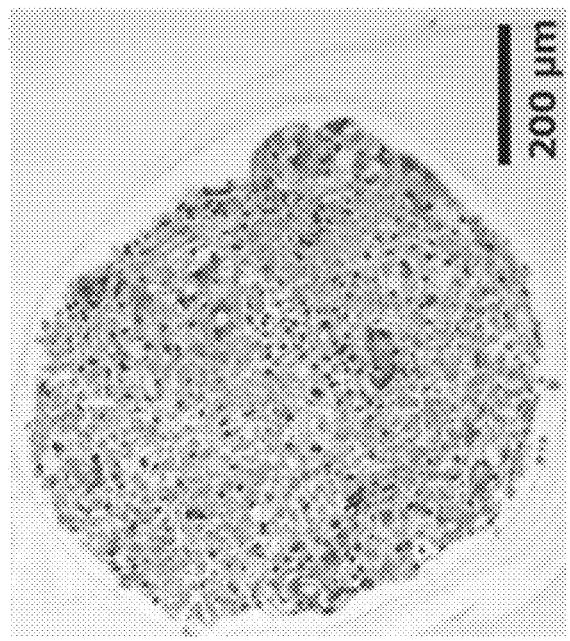
Figure 5:
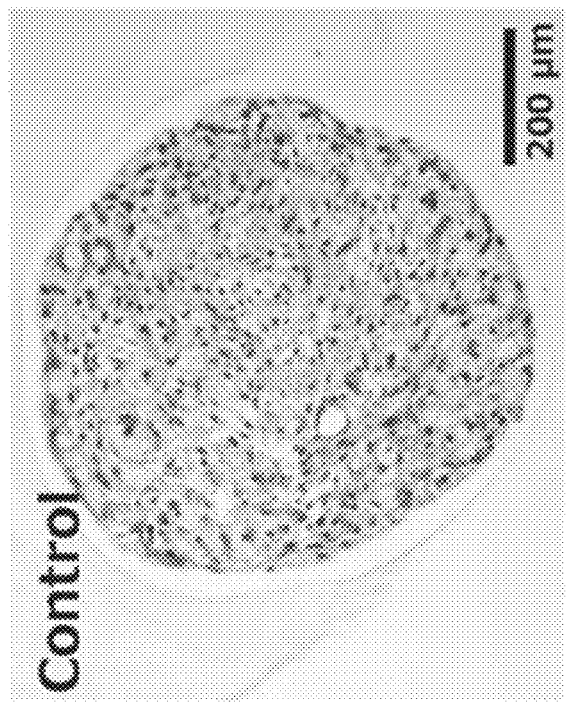

FIG. 5 Immunostaining images of the human liver-like three-dimensional constructs described in Experimental example 5.

Figure 6:
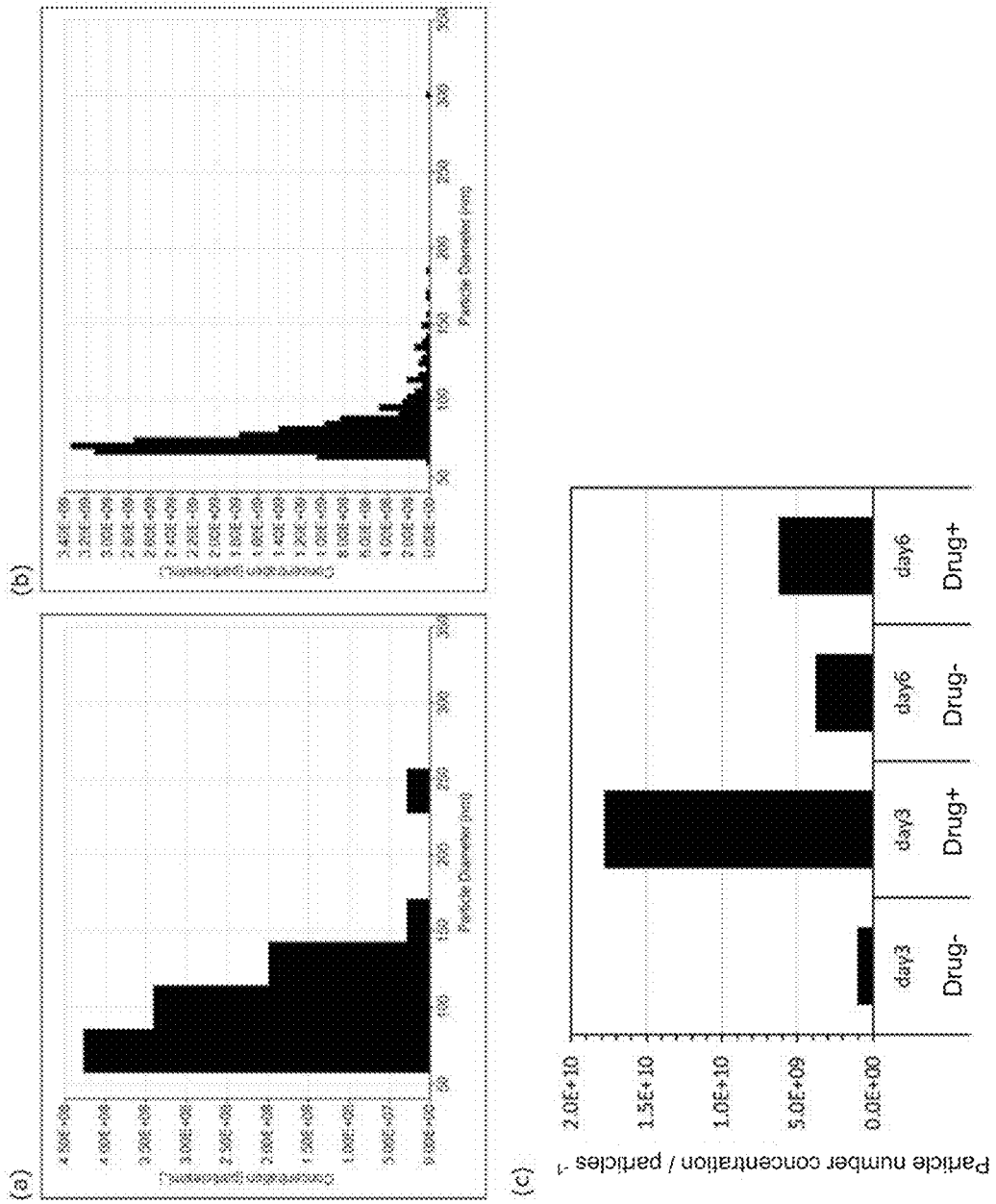

FIG. 6 Graphs showing results from determining the number and the particle-size distribution of the exosome particles described in Experimental example 6.

Figure 7:
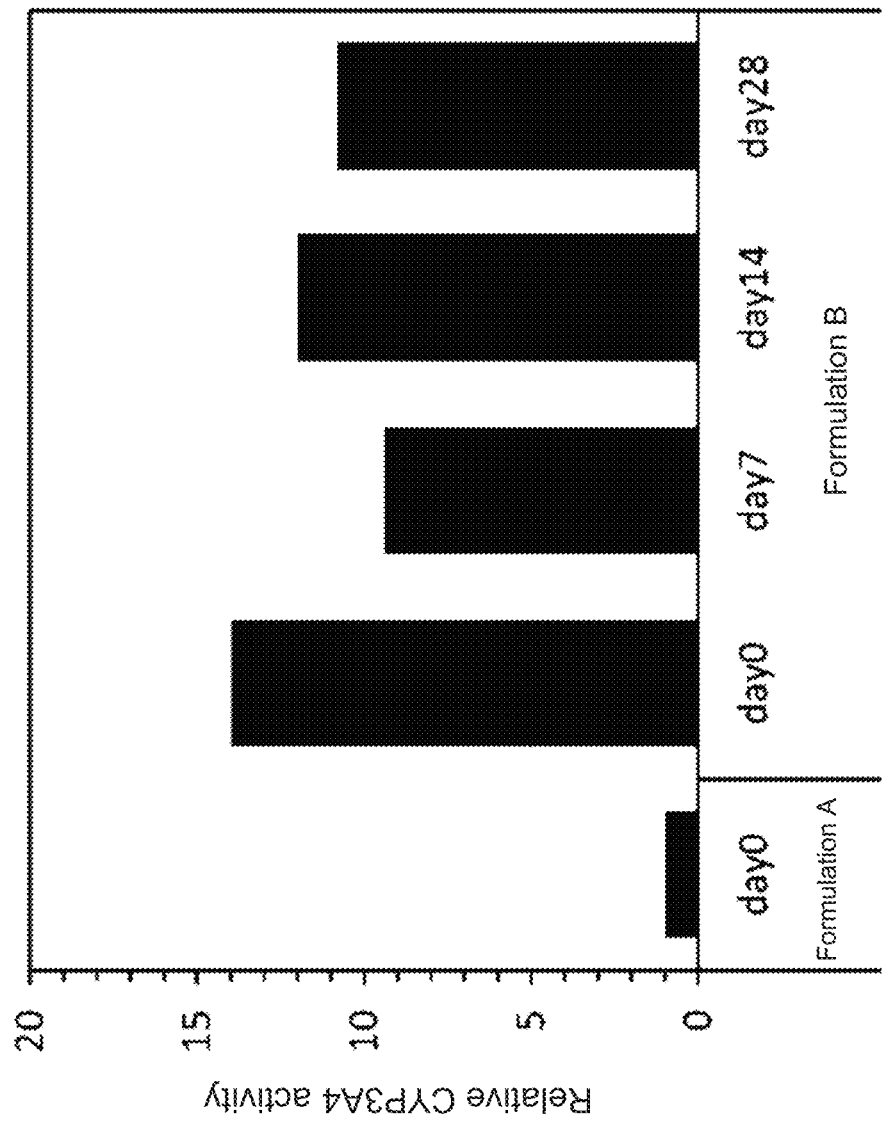

FIG. 7 A graph showing CYP3A4 enzyme activity in the human liver-like three-dimensional construct A described in Experimental example 4'.

Figure 8:
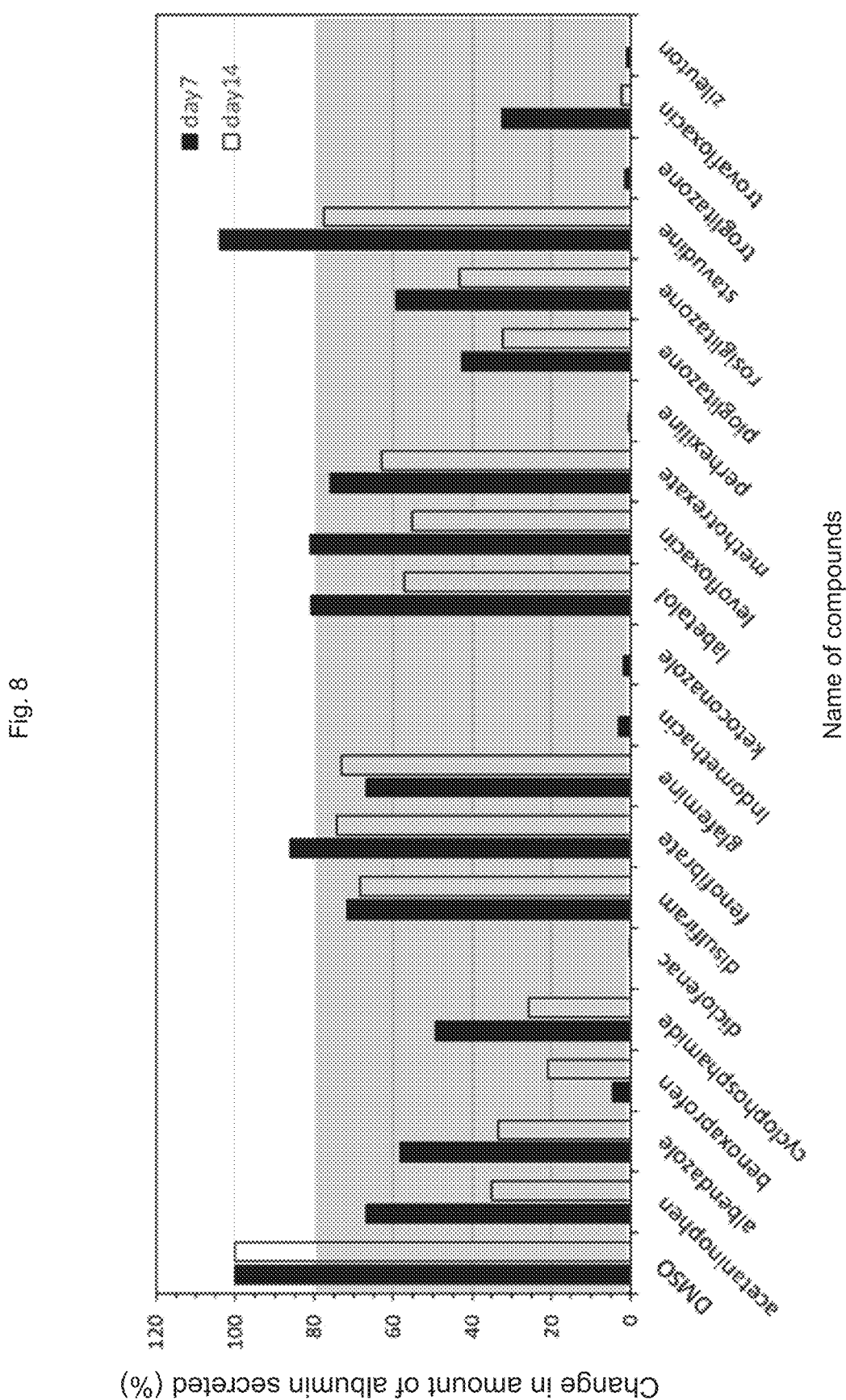

FIG. 8 A graph showing results from toxicity detection in Experimental example 5'.

Figure 9:
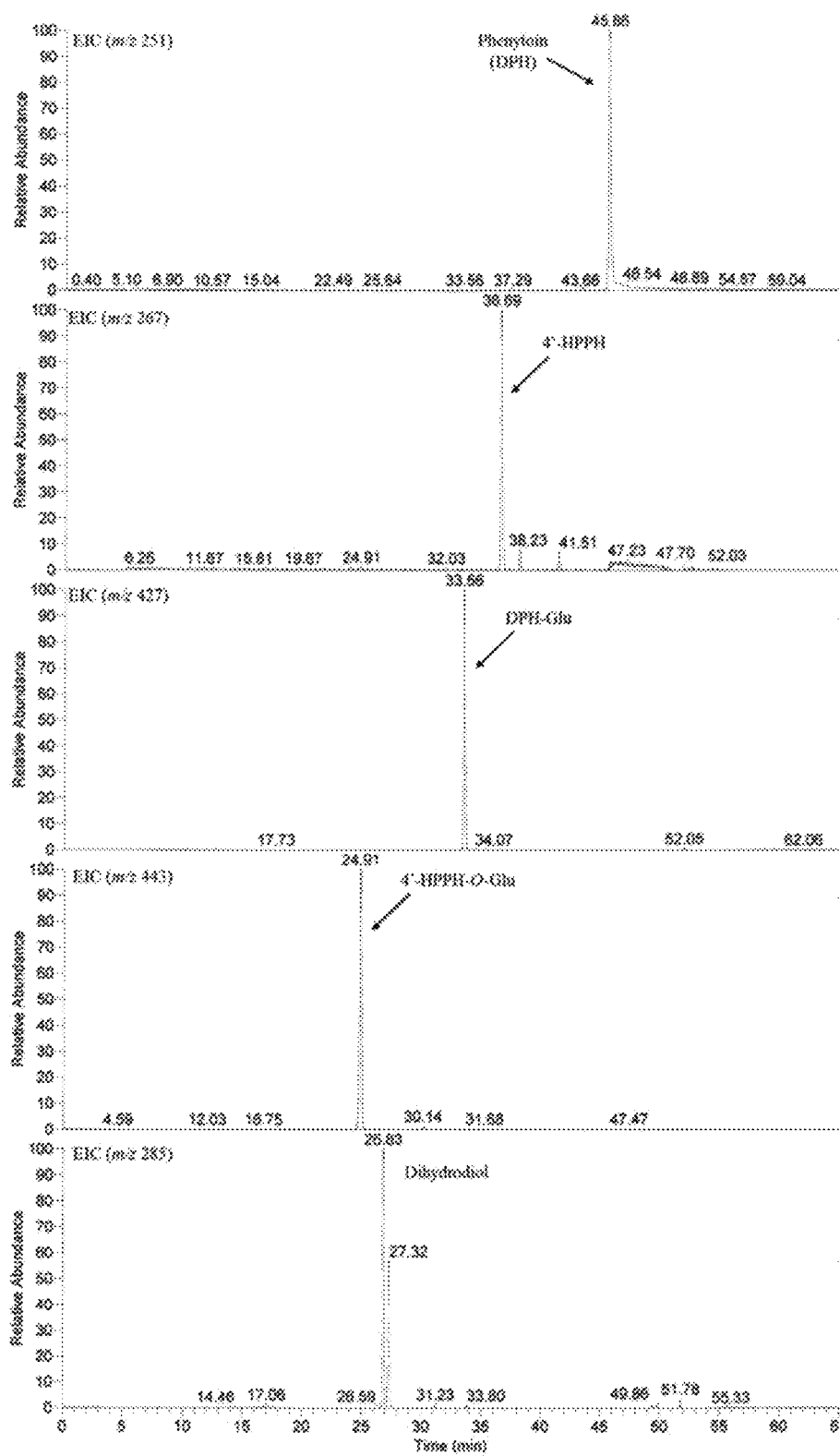

FIG. 9 Mass chromatograms of the respective metabolic products obtained when phenytoin was given to the human liver-like three-dimensional construct described in Experimental example 7.

Figure 10:
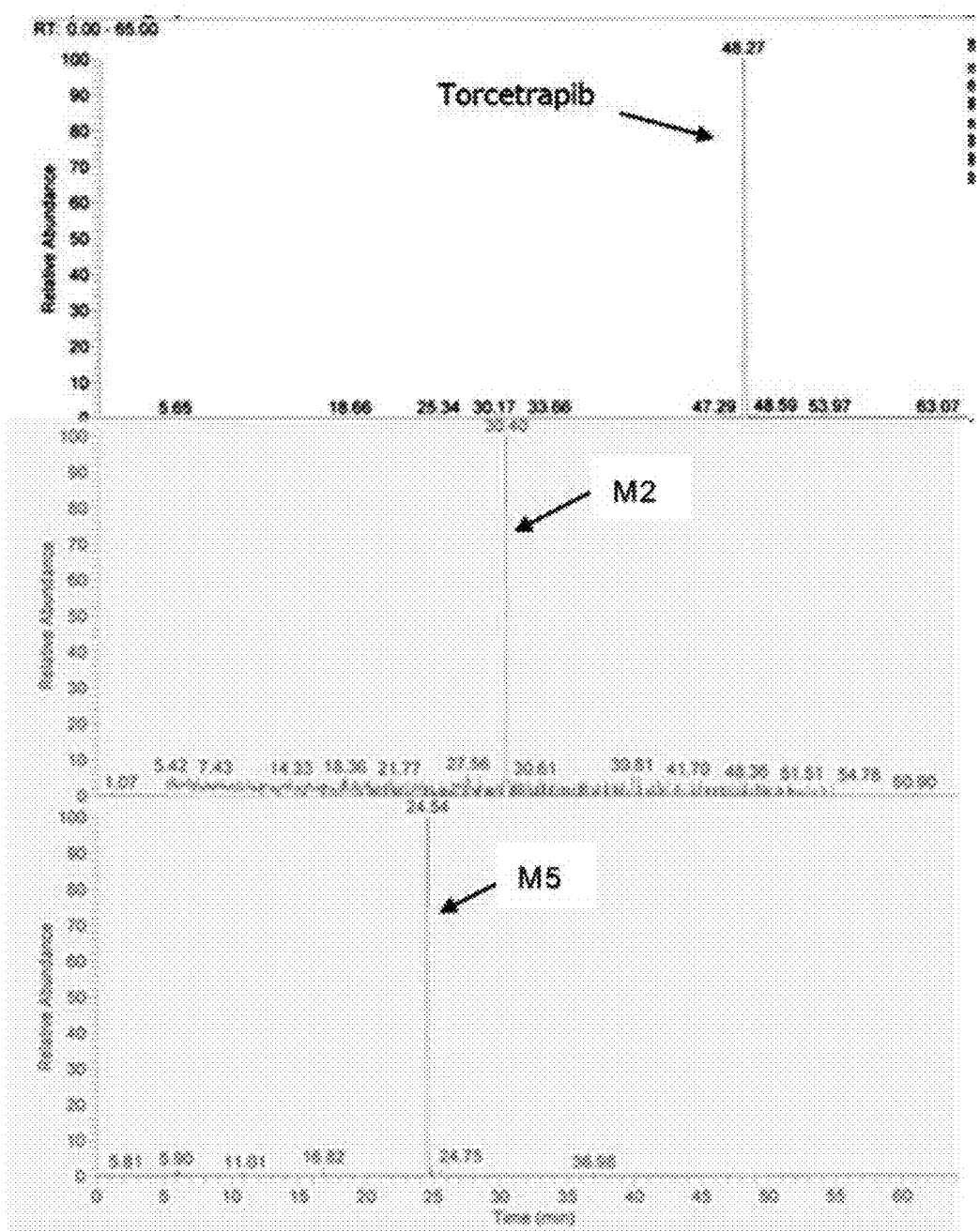

FIG. 10 Mass chromatograms of the respective metabolic products obtained when Torcetrapib was given to the human liver-like three-dimensional construct described in Experimental example 8.

MODES FOR CARRYING OUT INVENTION

Hereinafter, the present invention will be described in detail. The following embodiment is an example for illustrating the present invention and is not intended to limit the present invention. The present invention can be carried out according to various embodiments without departing from the scope of the invention.

All of the documents, patent application publications, patent publications and other patent documents cited herein are incorporated herein by reference.

The present invention relates to a human liver-like three-dimensional construct comprising a heterospheroid formed of an aggregate of human hepatocytes and human-derived cells other than the human hepatocytes. The heterospheroid contains human-derived cells and is free of mouse-derived cells. According to the present invention, a human liver model with high liver functions can be fabricated by simply co-culturing human hepatocytes and other human-derived cells such as human hepatic stellate cells.

1. Culture Conditions

According to the present invention, a spheroid comprising a mixture of hepatocytes and human-derived cells is prepared by co-culturing the human-derived hepatocytes (first cells) and the human-derived cells other than said hepatocytes (second cells). Since the prepared spheroid is composed of a mixture of different kinds of cells, this spheroid is called a "heterospheroid" (but also simply referred to herein as a "spheroid").

The hepatocytes (also called Hep) used in the present invention refer to human-derived cells such as biopsied hepatocytes, commercially available cryopreserved hepatocytes or the like. Alternatively, induced hepatocytes, reprogrammed hepatocytes or the like derived from ES cells, iPS cells, organism-derived cells or the like using a reagent, a gene, mRNA, microRNA or the like can also be used.

Meanwhile, the human-derived cells other than the human hepatocytes used as the second cells in the present invention are at least one kind selected from the group consisting of human hepatic stellate cells, human pulmonary fibroblasts, human aortic adventitial fibroblasts, human periodontal ligament fibroblasts, human intestinal myofibroblasts, human tenocytes, human astrocytes, human neonatal dermal fibroblasts, human synovial stromal cells, human brain capillary pericytes, human kidney mesangial cells, human cardiac fibroblasts, human aortic smooth muscle cells, human osteoblasts, normal human skeletal muscle cells, human dental pulp stem cells, human nucleus pulposus cells, human annulus fibrosus cells, human ligament cells, human chondrocytes, human Kupffer cells, human sinusoidal endothelial cells, human biliary epithelial cells, human adult dermal fibroblasts, human bone marrow-derived mesenchymal stem cells and human adipose-derived mesenchymal stem cells. These second cells can be either normal or pathogenic. The second cells may be induced cells or reprogrammed cells derived from ES cells, iPS cells, organism-derived cells or the like using a reagent, a gene, mRNA, microRNA or the like. Alternatively, they may be commercially available cells or may be prepared from a human tissue by an enzymatic or physical treatment.

The second cells preferably comprise at least one kind selected from the group consisting of human hepatic stellate cells, human Kupffer cells, human sinusoidal endothelial cells, human biliary epithelial cells, human adult dermal fibroblasts and human adipose-derived mesenchymal stem cells, and particularly preferably comprise human hepatic stellate cells.

The above-described first cells and second cells separately cultured or maintained in media suitable to the respective cells are mixed. When the mixture of the first and second cells is cultured, the cells cluster together and form a cell aggregate, namely, a heterospheroid.

According to the present invention, the culture medium for the first cells may be a medium generally employed for culturing hepatocytes. Examples of such a medium include DMEM, RPMI-1640, DMEM/F12 and Williams' Medium E. Examples further include commercially available hepatocyte culture media (Primary Hepatocyte Maintenance Supplements (CM series, Life Technologies)).

Furthermore, a medium for the second cells can suitably be selected according to the kind of the cells. For example, OGM Bullet Kit (Lonza) can be used as a culture medium for human osteoblasts (NHOST), Tenocyte Growth Medium (Zenbio) can be used as a culture medium for normal human tenocytes (TEN), CSC Complete Recombinant Medium (Cell Systems Corporation) can be used as a culture medium for normal human brain capillary pericytes (HBMPC), Intra-Hepatic Biliary Epithelial Cell Growth Medium (Zenbio) can be used as a culture medium for normal human biliary epithelial cells (IHBEC), and Prigrow I (Applied Biological Materials Inc.) can be used as a culture medium for normal human sinusoidal endothelial cells (SEC).

The medium may be supplemented, for example, with an antibiotics or a serum such as fetal bovine serum.

Herein, "mixing" is not particularly limited as long as the first cells and the second cells are in contact with each other. Examples include: (i) an aspect in which cell suspensions of the respective cells are placed in one container to be mixed with each other; (ii) an aspect in which a cell suspension of either one of the first or second cells is added to a culture container of the other cells; and (iii) an aspect in which a medium of either one of the cells is completely or partially removed after the cells are attached to or settled in a culture container, and a cell suspension of the other cells is added to this culture solution.

The mix ratio of the cells used for preparing the heterospheroid is determined such that the number of the first cells (hepatocytes) is larger than the number of the second cells (human-derived cells other than the hepatocytes). The ratio of the second cells to the first cells (second cells/first cells) is preferably 0.01-1.0, more preferably 0.01 or higher but lower than 1, still more preferably 0.02-0.5, and most preferably 0.05-0.1.

The concentration of the first cells in the co-culture medium is preferably at least $0.4 \times 10^5$ cells/ml or more, more preferably $0.6 \times 10^5$-$2.0 \times 10^5$ cells/ml, and most preferably $0.8 \times 10^5$-$1.2 \times 10^5$ cells/ml. Preferably, the second cells are prepared such that their number gives the above-described ratio with respect to the cell number of these first cells, and these first and second cells are mixed.

The above-mentioned concentration range refers to the concentration before the start of co-culture.

3. Measurements and Selection Indicator

Spheroid-forming capacity can be examined by a morphological examination using an optical microscope.

Furthermore, whether or not a spheroid has a function of interest can be examined using a gene expression in the spheroid as an indicator. While the gene used as an indicator is not particularly limited, it is preferably a liver function-related gene, a drug metabolism-related gene or the like. Preferable examples of the drug metabolism-related gene include CYP1A2, CYP2A6, CYP2B6, CYP2C9, CYP2C19, CYP2D6, CYP3A4, CYP2E1, GSTM1, GSTT1, SULT2A1, UGT1A1, UGT2B4, BCRP, BSEP, MRP2, MATE1, MRP6, MDR1, NTCP, OCT1, OATP1B1 and OATP1B3. Examples of the liver function-related gene include HNF1A, HNF3A, HNF4A, HNF6, PROX1, CEBPA, CAR and ALB. The drug metabolism-related genes and the liver function-related genes are, however, not limited to these examples.

The method for confirming the gene expression can be carried out by a general technique, for example, RT-PCR, Northern blotting or the like which can be employed alone or in a suitable combination.

Alternatively, whether or not the spheroid has the function of interest can be assessed using an ATP level, albumin secretion, ammonium metabolism, urea production, drug metabolism, protein expression or the like as an indicator.

4. Production of Human Liver-Like Three-Dimensional Construct

According to the present invention, the spheroids formed as described above can be blended or stacked to fabricate a human liver-like three-dimensional construct.

The method for blending or stacking the spheroids in a three-dimensional manner is not particularly limited. An example of the method for blending the spheroids in a three-dimensional manner include a method in which the spheroids are placed and cultured in a tube or the like. By doing so, the spheroids will fuse with each other and form a larger mass of spheroids, thereby forming a human liver-like three-dimensional construct of the present invention.

Alternatively, a method is known in which spheroids are disposed and stacked in a predetermined three-dimensional space to fabricate a three-dimensional cell construct (WO2008/123614). According to this method, needles are aligned on a substrate in a Kenzan (spiky flower frog)-like manner, on which spheroids are disposed by skewering the cell masses on the needles or piercing the needles through the cell masses. Accordingly, this method can provide a scaffold-free three-dimensional construct.

Herein, "stacking" means to arrange a total of two or more (preferably nine or more) spheroids in the length, width and height directions to form a construct.

According to the present invention, a liver-like three-dimensional construct is preferably fabricated by a method using the above-described needles. Since automatic stacking robots for realizing the above-described method are already known (Biotechnology 3D printer "Regenova" (registered trademark) and "S-PIKE" (registered trademark), both available from Cyfuse Biomedical K. K.), it is preferable to use these robots.

Hereinafter, a preferred example of the above-described method will be briefly described. According to this preferred exemplary method, automatic stacking robot "Regenova" (registered trademark) is used to fabricate a human liver-like three-dimensional construct of the present invention by following, for example, Steps I-IV.

In Step I, the above-described spheroids are prepared. The provided spheroids preferably have a projected area (equivalent circular) diameter of preferably 300-1000 μm, more preferably 300-800 μm, and particularly preferably 400-600 μm.

A projected area (equivalent circular) diameter is an equivalent circular diameter of a projected area observed with an optical microscope. If the above-described automatic stacking robot is employed, the measuring means mounted on the device can be used for the measurement. In other cases, a stereomicroscope can be used for the measurement.

Steps II and III employ an approach of fabricating a construct precursor by Kenzan-type bioprinting. In Step II, spheroids are stacked using a Kenzan (made of, for example, stainless steel, tungsten) having needles aligned at a predetermined pitch.

Step III is a perfusion culture process that is carried out while spheroids are skewered on the Kenzan, by which the stacked spheroids fuse with each other and form a dice, patch or a like bioprinted construct. The flow rate of the medium in the perfusion culture process is preferably 1-4 ml/min. For the perfusion culture, a specialized circulating culture device (for example, perfusion culture vessel type 1 PC1004 (trade name) manufactured by Cyfuse Biomedical K. K.) is preferably used from the viewpoint of efficiently supplying the medium component.

In Step IV, after confirming that the spheroids are fused with each other at the end of the above-described perfusion culture, the construct precursor is pulled out from the Kenzan and the pulled out construct precursor is subjected to shake culture, thereby obtaining a human liver-like three-dimensional construct of interest.

Steps I-IV described above are merely an example and the contents of the steps may be modified, omitted or added as long as a human liver-like three-dimensional construct of the present invention is obtained.

For example, in Step II, instead of skewering the spheroids on the Kenzan, the Kenzan can be pierced into the spheroids. In Step III, shake culture may be employed instead of perfusion culture. Also in Step III, the culture system may be subjected to ultrasonic irradiation upon the culture process. In Step IV, shake culture or perfusion culture may be carried out directly without pulling out the construct from the Kenzan.

The number and the shape of the disposed spheroids are not particularly limited and they are discretionary.

In a case where human hepatic stellate cells are used as the second cells, a stellate-cell quiescence agent that promotes transition of the human hepatic stellate cells from an active state into a quiescent state (also referred to as an inactive state) is preferably added to the medium component upon production.

Herein, a quiescent state refers to a state where the cells do not undergo cell divisions. Cells in the G0 phase of the cell cycle are deemed to be in a quiescent state.

Human hepatic stellate cells are fibroblasts present in a space between hepatocytes and sinusoidal endothelial cells, called space of Disse, in the liver of a human body. Human hepatic stellate cells are distinguished from other cells in the liver in that they express molecules such as: a receptor, platelet-derived growth factor receptor-β (PDGFRβ); an enzyme, lecithin retinol acyltransferase (LRAT); cytoskeletal proteins, desmin and glial fibrillary acidic protein; a transcription factor, heart-and neural crest derivatives-expressed protein; a globin, cytoglobin (CYGB); and the like. The hepatic stellate cells are activated upon liver damage and primary culture, and transform into myofibroblast (MFB)-like cells. In the liver of a human body, the activated hepatic stellate cells proliferate, take part in inflammatory responses, and overproduce ECM while producing a fibrosis inducer such as TGF (transforming growth factor)-β by themselves, playing a key role in the fibrotic response. In a human body, stellate cells in a normal liver with no inflammation are in a quiescent state.

Human hepatic stellate cells are in an active state under normal culture conditions. Specifically, human hepatic stellate cells are highly proliferative and show fibrosis under usual culture conditions, and they are in a state comparable to a state where some kind of inflammation is occurring in a liver of a living body. Hence, for use in the hepatotoxicity assessment, the human liver-like three-dimensional construct of this aspect is preferably in a state similar to that of a normal liver.

Although ECM production facilitates formation of a human liver-like three-dimensional construct, an excessive amount of ECM present in the human liver-like three-dimensional construct after achieving the construct may have a risk of affecting the hepatotoxicity assessment and the like.

Therefore, a stellate-cell quiescence agent is preferably used to ensure that the human stellate cells are in a quiescent state during the production of a human liver-like three-dimensional construct.

According to the present invention, a cell quiescence agent can be selected from a group consisting of compounds that are known as stellate-cell quiescence agents (deactivators). Examples include TGFβ inhibitors A83-01, SB-431542, SB-505124 and SB-522334; an angiogenesis inhibitor TNP-470; a LDHA inhibitor FX-11; a glycolytic inhibitor 2 deoxyglucose; and the like.

The stellate-cell quiescence agent can be added at any timing between the beginning of the spheroid formation to the hepatotoxicity assessment, depending on the kind thereof, the culture conditions and the like. However, while the stellate cells take time to enter the quiescent state after the addition of the quiescence agent, if the timing of entering the quiescent state is too early, the activity of the construct is high immediately after the production but durability of this activity may not last. Therefore, the quiescence agent is preferably added later than two days after the start of the spheroid formation but before the hepatotoxicity assessment.

In the case of the preferred exemplary method comprising Steps I-IV described above, the stellate-cell quiescence agent is particularly preferably added at the following timing.

Two days after the start of the spheroid formation in Step I;

The beginning of Step III; or

The beginning of shake culture of the construct precursor pulled out from the Kenzan in Step IV.

The concentration of the stellate-cell quiescence agent in the medium is preferably in a range of 0.1-3 (μmol/l).

The stellate cells require some time for entering the quiescence state after the addition of the stellate-cell quiescence agent (usually about 2-7 days depending on the culture conditions). Therefore, if the medium is exchanged during this period, it is preferably exchanged with a medium supplemented with a stellate cell quiescent agent.

In order to confirm that the quiescent state of the stellate cells is achieved, expression of α-SMA (ACTA2), a gene in the spheroids or the construct, is preferably used as a marker. In this case, the hepatic stellate cells are judged to have entered the quiescent state if the α-SMA gene expression level is decreased to $1/10$-$1/100$ compared to that before the addition of the quiescence agent. Transition of the hepatic stellate cells into the quiescent state is preferably completed before the hepatotoxicity assessment.

5. Human Liver-Like Three-Dimensional Construct

The human liver-like three-dimensional construct of the present invention can be produced in a scaffold-free manner, where the cells can adhere to each other directly or via an extracellular matrix or E-cadherin. The extracellular matrix of the human liver-like three-dimensional construct of the present invention preferably contains 1-3 mass % type I collagen and 1-3 mass % type III collagen based on dry weight. When the adhesion is mediated by E-cadherin, E-cadherin tends to be localized at the boundary between the hepatocytes or at a joint of a bile duct-like construct or the like.

The extracellular matrix and E-cadherin both originate from the cells composing the human liver-like three-dimensional construct.

Furthermore, the human liver-like three-dimensional construct of the present invention has more first cells than second cells at the end of the production, where the ratio of the number of the second cells (other human-derived cells) to the number of the first cells (human hepatocytes) is 0.01 or higher but lower than 1, preferably 0.01-0.1, and more preferably 0.01-0.05.

Preferably the first cells and the second cells are homogeneously distributed in the human liver-like three-dimensional construct of the present invention by adjusting the co-culture conditions, the kinds of cells used and the like. More preferably, the first cells and the second cells are homogeneously distributed under the conditions where the second cells comprise human hepatic stellate cells.

Whether or not the first cells and the second cells are homogeneously distributed can be judged by the following method. Specifically, the human liver-like three-dimensional construct is fixed with formalin and embedded in paraffin to prepare a tissue block. A section is cut out from the obtained block to prepare a tissue section. The obtained tissue section is subjected to HE staining and immunostaining, and the images are taken. For immunostaining, a primary antibody that recognizes the first cells and a primary antibody that recognizes the second cells can be used. For example, for hepatocytes, an anti-albumin antibody is preferably used. If the second cells contain hepatic stellate cells, an anti-desmin antibody that recognizes hepatic stellate cells is preferably used. Referring to the obtained stain image, the areas of the first cell region and the second cell region are measured to calculate the area ratio R between the first cell regions and the second cell regions in every 200 μm×200 μm region.

$$R=(\text{Area of second cells})/\{(\text{Area of second cells})+(\text{Area of first cells})\}\times 100(\%)$$

The first cells and the second cells are judged to be homogeneously distributed if the histogram of the area ratio R (%) measured in each region shows dispersion that follows normal distribution and the standard deviation (σ) of R is less than 3.0, in particular 1.5-2.0.

Moreover, provided that the histogram of the area ratio R shows dispersion following the normal distribution and σ satisfies the above-described numerical range, a cluster of the second cells such as human hepatic stellate cells particularly preferably has a maximum projected area (equivalent circular) diameter of 100 μm, in particular 20-100 μm.

Although the human liver-like three-dimensional construct of the present invention can be produced in a scaffold-free manner, it can have a large size. According to the above-described preferred production method, a large human liver-like three-dimensional construct can be fabricated in a scaffold-free manner.

For example, if the human liver-like three-dimensional construct of the present invention is fabricated to have a substantially spherical shape, the projected area (equivalent circular) diameter is preferably at least 1.0 mm, more preferably 1.1-10.0 mm and particularly preferably 1.2-5.0 mm.

If the human liver-like three-dimensional construct of the present invention is fabricated to have a hollow or solid substantially round cylindrical shape, the average diameter of the cross sections (in case of a hollow shape, the average diameter of the outer peripheries of the cross sections) cut at three places at equal intervals in the longitudinal direction is preferably 1.0-10.0 mm and more preferably 1.2-5 mm. If the construct has a deformed shape such as an ellipse or the like, the length of the minor axis of the cross section is measured as the "diameter of the cross section".

If the human liver-like three-dimensional construct of the present invention is fabricated to have a hollow or solid substantially polygonal cylindrical shape, the average diameter of the circumscribed circles of the cross sections (in case of a hollow shape, the outer peripheries of the cross sections) cut at three places at equal intervals in the longitudinal direction is preferably 1.0-10.0 mm and more preferably 1.2-5 mm. If the outer circumference has a deformed shape such as an ellipse or the like, the length of the minor axis of the outer circumference is measured as the "diameter of the outer circumference."

If the human liver-like three-dimensional construct of the present invention has a ring shape, the average diameter of the outer circumferences at the bottom and at the top is preferably 1.0-10.0 mm and more preferably 1.2-5 mm. If the outer circumferences have a deformed shape such as an ellipse or the like, the length of the minor axis of the outer circumference is measured as the "diameter of the outer circumference."

Herein, a ring shape refers to a shape where the length of the body is shorter than the diameter of the outer circumference at the bottom. If the length of the body is equal to or longer than the diameter of the outer circumference at the bottom, the shape of the construct is classified as a hollow round cylinder.

The human liver-like three-dimensional construct of the present invention can be fabricated to have a sheet shape by aligning the heterospheroids in the horizontal direction. Since the heterospheroids are larger than the size of the cell alone, a sheet obtained by aligning the heterospheroids in the horizontal direction is a three-dimensional sheet with a certain thickness. The average thickness of this sheet is preferably at least 300 μm, more preferably at least 500 μm, and particularly preferably 500-1000 μm. The thickness can be measured with an optical microscope.

Whether or not the human liver-like three-dimensional construct of the present invention can serve as a liver model can be judged by a technique similar to the technique described in section "3. Measurement and selection indicator" above, which uses selection indicators in the spheroids. The genes used as the indicators are preferably: genes of phase 1 enzymes involved in drug metabolism such as CYP3A4, CYP1A2, CYP2D6 and CYP2C9; genes of phase 2 enzymes involved in drug metabolism such as UGT1A1; and transporter genes such as OATP1B1 and OATP1B3.

As another indicator specific to the human liver-like three-dimensional construct, the oxygen concentration inside the construct can be monitored using a fluorescent detection probe (MAR, Goryo Chemical, Inc.).

Moreover, based on the finding that exposure to rifampicin enhances expression of CYP3A4 enzyme in the hepatocytes in vivo, rifampicin can be brought into contact with the human liver-like three-dimensional construct to confirm the expression level of CYP3A4.

The human liver-like three-dimensional construct of the present invention maintains functions similar to those of a human liver even after a long-term culture, and also has a high survival rate.

The human liver-like three-dimensional construct of the present invention can be used as a liver model for various usages such as assessment of metabolism of a test substance in a human body, assessment of hepatotoxicity of a test substance to a human, and the like.

For example, for metabolism assessment, a test substance described later can be brought into contact with the human liver-like three-dimensional construct of the present invention, and when a metabolite of the test substance is detected as a reaction product inside or outside the construct, the test substance is judged to have been metabolized. Examples of the metabolite of the test substance include phase I and phase II metabolites of the test substance. Detection can be carried out, for example, by a known technique such as LC/MS/MS.

Preferably, the human liver-like three-dimensional construct of the present invention contains human hepatic stellate cells as the second cells and the human hepatic stellate cells are in a quiescent state.

The human liver-like three-dimensional construct of the present invention is preferably used in a method for assessing hepatotoxicity of a test substance to a human.

5. Human Liver-Like Complex

While the human liver-like three-dimensional construct of the present invention can be applied directly to various usages, two or more of the human liver-like three-dimensional constructs can be attached and fused with each other to give a human liver-like complex. The human liver complex of the present invention can be applied to usages similar to the usages of the human liver-like three-dimensional construct.

6. Method for Assessing Hepatotoxicity

The method for assessing hepatotoxicity of a test substance to a human may be, for example, a method comprising the following steps (1) and (2). Hereinafter, this method may also be referred to as a "hepatotoxicity assessment method of the present invention."

(1) A contact step in which a test substance is brought into contact with the human liver-like three-dimensional construct of the present invention.

(2) A determination step in which presence or a degree of damage to the human liver-like three-dimensional construct of the present invention is determined.

The test substance used in the hepatotoxicity assessment method of the present invention is not particularly limited. For example, a natural compound; an organic compound; an inorganic compound; a polymer compound; a protein; a peptide; a compound library; expressed products of a gene library; a cell extract; a cell culture supernatant; a fermenting microorganism product; a marine organism extract; a plant extract; or the like, a drug containing any of them, a xenobiotic such as a food additive, or the like can be used. Herein, a "xenobiotic" comprises any substance that is foreign to an organism. In addition, a xenobiotic and a liposome or a synthetic polymer can be used to examine a drug delivery system.

Examples of the drug include low-molecular-weight drugs with a molecular weight of 2,000 or less; moderate-molecular-weight drugs having a molecular weight of more than 2,000 (about several thousands) or composed of some peptides; high-molecular-weight drugs obtained by conjugating an antibody drug and a polymer; nucleic acid drugs such as an antisense oligonucleotide, RNAi, an aptamer, a decoy or the like; cell drugs typified by somatic stem cells; and the like.

Examples of a specific drug compound include rifampicin, dexamethasone, phenobarbital, ciglitazone, phenytoin, efavirenz, simvastatin, β-naphthoflavone, omeprazole, clotrimazole, 3-methylcholanthrene, acetaminophen, trovafloxacin, estrone, nifedipine, diclofenac, indometacin, methotrexate, troglitazone, CCl4, paracetamol, halothane, amiodarone, thioridazine, methyldopa, isoniazid, levofloxacin, stavudine, felbamate, cyclophosphamide, pioglitazone, rosiglitazone, ketoconazole, perhexilline, benoxaprofen, acetaminophen, clomipramine, fenofibrate, imipramine, zileuton, troglitazone, albendazole, fluconazole, graphemin, grisoflavin and labetalol.

In the contact step (1), the human liver-like three-dimensional construct and a test substance are usually brought into contact with each other by adding the test substance to a medium or a culture solution, but the present invention is not limited to this method. In a case where the test substance is a protein or the like, a DNA vector that expresses said protein can be introduced into the cell to conduct the contact step.

In the determination step (2), presence or a degree of damage to the human liver-like three-dimensional construct of the present invention is determined. +The presence or the degree of damage can be determined, for example, by using a survival rate of hepatocytes, a liver damage marker or an exosome as an indicator. Moreover, it can also be confirmed by HE staining or antibody staining.

For example, a test substance can be added to a culture solution of the human liver-like three-dimensional construct so that when the survival rate of the cells in the human liver-like three-dimensional construct is decreased, the test substance is judged to be hepatotoxic. If no significant change is seen in the survival rate, the test substance is judged to have no hepatotoxicity. The survival rate can be confirmed, for example, by measuring the ATP activity.

Examples of the liver damage marker include ALT, AST, albumin and urea. For example, if ALT or AST in a culture solution of the human liver-like three-dimensional construct is increased after addition of a test substance to the culture solution, the test substance is judged to be hepatotoxic. If no significant change is seen in ALT or AST, the test substance is judged to have no hepatotoxicity. Moreover, if the amount of albumin or urea in a culture solution of the human liver-like three-dimensional construct is decreased after addition of a test substance to the culture solution, the test substance is judged to be hepatotoxic. If no significant change is observed in the amount of albumin or urea, the test substance is judged to have no hepatotoxicity.

Exosomes are nano-sized membrane vesicles with a diameter of about 30-100 nm, which are released from cells in vivo. Presence or a degree of hepatotoxicity can be determined by monitoring the number, size, inclusion component and the like of the exosomes released in the medium.

Examples of the inclusion component targeted for the monitoring include miRNAs and proteins. In particular, miRNAs contained in disease-specific exosomes collected from blood have already been reported to have relationship with pathology and progression in cancers, chronic hepatitis C and the like, and have been considered of their use as disease-related biomarkers. Since miRNAs are involved in events caused in cells, they can favorably be used as a means for judging presence or a degree of hepatotoxicity.

The miRNA targeted by the analysis is not particularly limited as long as the amount thereof secreted from the cells alters with the degree of hepatotoxicity. Moreover, the miRNA can suitably be selected according to the kind of cells and the like.

For example, in a case where human hepatic stellate cells are used as the second cells, i.e., the human liver-like three-dimensional construct contains human hepatocytes and human hepatic stellate cells, amounts of miRNAs comprising the nucleotide sequences represented by SEQ ID NOS:1-6, i.e., miR-122, miR-192 and miR-224, secreted in culture supernatants increase with hepatotoxicity as described in the examples below.

TABLE 1

| Name of miRNA | Sequence | SEQ ID NO: |
|---|---|---|
| miR-122-5p | uggagugugacaaugguguuug | 1 |
| miR-122-3p | aacgccauuaucacacuaaaua | 2 |
| miR-192-5p | cugaccuaugaauugacagcc | 3 |
| miR-192-3p | cugccaauuccauaggucacag | 4 |
| miR-224-5p | ucaagucacuaguggguuccguuuag | 5 |
| miR-224-3p | aaaauggugcccuagugacuaca | 6 |

One or more of the miRNAs can be measured as indicators for judging presence or a degree of hepatotoxicity.

Measurement of a miRNA in exosomes released from the cells include, for example, the following steps:

(2-1) Exosome collection step in which exosomes released from the three-dimensional construct are collected.

(2-2) miRNA analysis step in which a miRNA contained in the exosomes is analyzed.

In the exosome collection step (2-1), for example, the culture supernatant is partially sampled and exosomes are collected from the sampled culture supernatant by a known technique such as ultracentrifugation or use of a commercially available exosome isolation kit.

In the miRNA analysis step (2-2), first, miRNAs are extracted from the collected exosomes by a known technique such as use of a commercially available miRNA extraction kit. Next, an expression level of a specific miRNA among all of the extracted miRNAs is measured utilizing a known technique such as a miRNA microarray technique or PCR typified by quantitative real-time PCR, digital PCR or the like.

The expression level of the specific miRNA that is known to increase or decrease with the degree of hepatotoxicity can be compared with the expression level of the miRNA secreted from cells that are not in contact with the test substance (reference level) to assess the degree of hepatotoxicity. Alternatively, other than the reference level, an appropriate threshold can be determined for each kind of miRNAs so as to judge the presence of hepatotoxicity by seeing if the level exceeds or falls below this threshold.

A miRNA microarray is favorable since expression profiles of a plurality of kinds of miRNAs can be confirmed concurrently.

In the miRNA collection step (2-2), a principal component analysis may be further conducted based on the sequence data of the miRNA expression levels detected for each of a plurality of kinds of test substances. For example, a correlation chart between a first principal component PC1 and a second principal component PC2 can be prepared to confirm correlation for each of the toxicity mechanisms of the test substances.

According to the hepatotoxicity assessment method of the present invention, hepatotoxicity can be confirmed even for a test substance which is clinically known to be hepatotoxic but its hepatotoxicity is not detectable by conventional methods.

EXAMPLES

Hereinafter, the present invention will be described specifically by means of experimental examples, although the present invention should not be limited to the following experimental examples.

Experimental Example 1 Fabrication of Precursor of Human Liver-Like Three-Dimensional Construct $1 \times 10^4$ cryopreserved human hepatocytes (manufactured by Sekisui XenoTech, LLC) and $5 \times 10^2$ human hepatic stellate cells (manufactured by ScienCell Research Laboratories) were seeded in each well of a spheroid formation plate which has been treated to minimize cell attachment (96-well microplate manufactured by Nunclon Sphera), and the resultant was cultured at 37° C. in 5% $CO_2$ for 3-5 days to give spheroids having a diameter (projected area (equivalent circular) diameter) of 500 μm.

Then, the resulting spheroids and a 3D cell stacking system Regenova (manufactured by Cyfuse Biomedical K. K.) were used to align a total of nine spheroids, three spheroids each in length and width directions, and they were cultured in a perfusion culture device for 5 days.

The nine spheroids fused with each other and formed one mass, thereby obtaining precursor A of a human liver-like three-dimensional construct.

Experimental Example 2 Fabrication of Precursor of Human Liver-Like Three-Dimensional Construct $1 \times 10^4$ cryopreserved human hepatocytes (manufactured by Sekisui XenoTech, LLC) and $5 \times 10^2$ human hepatic stellate cells (manufactured by ScienCell Research Laboratories) were seeded in each well of a spheroid formation plate which has been treated to minimize cell attachment (96-well microplate manufactured by Nunclon Sphera), and the resultant was cultured at 37° C. in 5% $CO_2$ for 3-5 days to give spheroids having a diameter (projected area (equivalent circular) diameter) of 500 μm.

Then, the resulting spheroids and a 3D cell stacking system Regenova (manufactured by Cyfuse Biomedical K. K.) were used to align a total of twenty-seven spheroids, three spheroids each in length, width and height directions, and they were cultured in a perfusion culture device for 5 days.

The twenty-seven spheroids fused with each other and formed one mass, thereby obtaining precursor B of a human liver-like three-dimensional construct.

Experimental Example 3 Fabrication of Human Liver-Like Three-Dimensional Construct by Shake Culture After pulling out the precursors A and B fabricated in Experimental examples 1 and 2 from the Kenzans, they were separately placed in 1 mL of medium dispensed in a Sarstedt 8-mL tube and shake cultured in a $CO_2$ incubator for 5 days.

Needle marks on the precursors from the Kenzan eliminated during the shake culture, and their shapes transformed into spheres, thereby obtaining human liver-like three-dimensional constructs A and B. The equivalent spherical diameter of the human liver-like three-dimensional construct A was 1.0 mm while the equivalent spherical diameter of the human liver-like three-dimensional construct B was 1.5 mm.

Experimental Example 3'

After pulling out the precursors A fabricated in Experimental example 1 from the Kenzans, they were separately placed in 1 mL of medium supplemented with a TGFβ inhibitor A83-01 to 3 μmol/l dispensed in a Sarstedt 8-mL tube, and shake cultured in a $CO_2$ incubator for 5 days. The resulting liver-like three-dimensional construct was called a liver-like three-dimensional construct A'.

Experimental Example 4 Gene Expression Analyses Using Liver-Like Three-Dimensional Construct As genes expressed in each of the human liver-like three-dimensional constructs A and B fabricated in Experimental example 3, CYP3A4, CYP1A2, CYP2C9, CYP2D6, UGT1A1, MRP2, BSEP, OATP1B1 and OATP1B3 were quantified by a real-time PCR technique.

The results obtained with the human liver-like three-dimensional construct A are shown in FIG. 1 while the results obtained with the human liver-like three-dimensional construct B are shown in FIG. 2. Each of the genes were persistently expressed in the human liver-like three-dimensional constructs A and B fabricated in Experimental example 3 as long as 20 days or longer following the fabrication and 30 days or longer following thawing of the cryopreserved hepatocytes as the raw material. On the other hand, cell death was caused in a monolayer culture 7-10 days after thawing.

The human liver-like three-dimensional constructs A and B fabricated in Experimental example 3 were found to be advantageous in that they can maintain extremely high levels of intrinsic liver functions that are responsible for metabolism, conjugation, cellular uptake and excretion for a long period of time.

Experimental Example 4' CYP3A4 Enzyme Activity of Human Liver-Like Three-Dimensional Construct A'

CYP3A4 enzyme activity in the human liver-like three-dimensional construct A' fabricated in Experimental example 3' was assessed with a CYP3A4 Activity Assay Kit (Bio Vision). The results are shown in FIG. 7. As a standard of comparison, results obtained with a formulation in which TGFβ inhibitor A83-01 was not added so that the stellate cells were not in a quiescent state are shown (Formulation A: corresponding to the human liver-like three-dimensional construct A fabricated in Experimental example 3).

The activity of CYP3A4 increased about 10 times by the addition of A83-01, and this enzyme activity remained at a high level, i.e., 70% or more of the initial value, even after 28 days. By making the stellate cells to be in a quiescent state, the metabolism functions of the liver construct were found to be further enhanced and maintained for a longer period of time.

Experimental Example 5 Assessment of Hepatotoxicity

A DMSO solution of trovafloxacin, a drug that is known to show hepatotoxicity when administered to a human, was prepared. The obtained drug-containing DMSO solution was added to the culture medium of the human liver-like three-dimensional construct A fabricated in Experimental example 3 such that the concentration of the drug in the medium was 5-1000 μmol/l. A control was prepared by adding only a DMSO solution to the culture medium of the human liver-like three-dimensional construct fabricated in Experimental example 3. Changes in the albumin concentrations in the media up to 24 days following addition of the drug, and the levels of ATP contained in the constructs at the end of the experiment were measured using CellTiter-Glo 3D substrate. Furthermore, tissue sections of the constructs were prepared to obtain images of HE staining and immunostaining for albumin.

Changes in the albumin concentrations in the media containing trovafloxacin are shown in FIG. 3. Moreover, difference in the levels of ATP contained in the human liver-like three-dimensional constructs are shown in FIG. 4. The immunostaining images of the human liver-like three-dimensional constructs are shown in FIG. 5.

A drug concentration-dependent decrease was observed in the albumin concentration, showing that drug toxicity was detectable. Since no decrease in the albumin concentration was observed in the monolayer culture system as a standard of comparison (details omitted), the toxicity assessment method of the present invention was shown to have superior toxicity assessment capability.

Experimental Example 5' Assessment of Hepatotoxicity

DMSO solutions of 20 kinds of drugs that were known to show hepatotoxicity upon administration to a human were prepared. The obtained drug-containing DMSO solutions were each added to the culture medium of the human liver-like three-dimensional construct A fabricated in Experimental example 3 such that their concentrations in the media were 20-50 times higher than the clinically reported maximum blood concentration (Cmax) of each drug in a human. A control was prepared by adding only a DMSO solution to the culture medium of the human liver-like three-dimensional construct fabricated in Experimental example 3. Changes in the albumin concentrations in the media 7 and 14 days following addition of the drug are shown in FIG. 8, in which data were normalized to the albumin concentration in the medium added with DMSO only (taken as 100%). After 14 days, statistical significance (80% or less) was observed in all compounds with respect to the medium added with DMSO only, showing excellent toxicity detection capability.

Experimental Example 6 Assessment of Hepatotoxicity Using Exosomes

The culture medium of Experimental example 5 was centrifuged at 4° C. and 2,000×g for 20 minutes, followed by centrifugation of the collected supernatant at 15,000×g for 30 minutes. To 2.2 mL of each collected sample solution, 1.1 mL of ExoCap Ultracentrifugation/Storage Booster (registered trademark) and 7.7 mL of ultrapure water were added. The resultant was homogeneously stirred and subjected to ultracentrifugation protocol (35,000 rpm, 70 minutes,4° C.). Following centrifugation, the supernatant was removed by decantation and with an aspirator, and the resultant was resuspended in an ExoCap Ultracentrifugation/Storage Booster (registered trademark) solution which was diluted 10-fold with ultrapure water to give 75 μL of each exosome solution.

The number and the particle-size distribution of the exosome particles were measured using qNano (nanoparticle multi-analyzer). In addition, expression of CD9 in the collected exosomes was confirmed by Western blotting. miRNAs contained in a sample extracted from the exosomes using a RNA extraction kit were measured by digital PCR. Furthermore, microRNAs contained in the exosomes were taken out and the amounts of miR-122, miR-192 and miR-1 were quantified by a quantitative PCR method. Here, miR-1 is a miRNA that is said to have no association with toxicity, and serves as a basis for judging the increase and the decrease of miR-122 and miR-192.

TABLE 2

| Name of miRNA | Sequence | SEQ ID NO: |
|---|---|---|
| miR-122-5p | uggagugugacaauggguguuug | 1 |
| miR-122-3p | aacgccauuaucacacuaaaua | 2 |
| miR-192-5p | cugaccaugaauugacagcc | 3 |
| miR-192-3p | cugccaauuccauaggucacag | 4 |
| miR-1-5p | acauacuucuuuauaugcccau | 7 |
| miR-1-3p | uggaauguaaagaaguauguau | 8 |

The results are shown in FIG. 6. FIG. 6(a) shows the particle-size distribution of the exosomes collected from the culture medium 3 days after the addition of DMSO only in Experimental example 5. FIG. 6(b) shows the particle-size distribution of the exosomes collected from the media 3 days after the addition of the trovafloxacin DMSO solution. FIG. 6(c) shows particle number concentrations of the exosomes collected under the respective conditions. An increase in the particle number concentration of the exosomes contained in the media was observed only three days after the drug addition. Furthermore, miR-122 was detected in the collected exosomes.

As drugs other than trovafloxacin, indometacin, diclofenac, benoxaprofen, zileuton and troglitazone were also added to the media. Results from digital PCR for determining the concentrations of miR-122-5p detected in the exosomes collected 3 and 10 days after the drug addition are shown in the following table. miR-122-5p was detected in all of the media added with these compounds, showing that the miRNA can serve as an indicator for toxicity assessment.

TABLE 3

| | miR-122-5p (copies/μl) | |
|---|---|---|
| Compound | Day 3 | Day 10 |
| Trovafloxacin | 99 | 552 |
| Indometacin | 125 | 149 |
| Diclofenac | 1190 | 42 |
| Benoxaprofen | 1013 | 123 |
| Zileuton | 505 | 165 |
| Troglitazone | 1460 | 117 |
| Blank | 0 | 0 |

Experimental Example 7 Chemical Construct Analysis of Metabolic Product of Phenytoin A DMSO solution of phenytoin was prepared. The obtained drug-containing DMSO solution was added to the culture medium of the human liver-like three-dimensional construct A' fabricated in Experimental example 3' such that the concentration of the drug in the medium was 10 μmol/l. The medium was sampled up to 6 days following the drug addition, and the metabolic products in the medium were subjected to separation and structural analysis by a LC/MS/MS method. Mass chromatograms of the respective metabolic products are shown in FIG. 9. Mass numbers used for identification of the detected peaks are shown in the following table. The abbreviations of the metabolites stand for the following constructs.

DPH; 5,5-diphenylhydantoin (phenytoin),
DPH-Glu; DPH-N-glucuronide,
4'-HPPH; (4'-hydroxyphenyl)phenylhydantoin,
4'-HPPH-O-Glu; (4'-hydroxyphenyl)phenylhydantoin-O-glucuronide.

TABLE 4

| Compound name | Molecular formula | Accurate molecular weight | Ion Mode |
|---|---|---|---|
| [DPH—H]⁻ | $C_{15}H_{11}N_2O_2$ | 251.0821 | Negative |
| [DPH-Glu-H]⁻ | $C_{21}H_{19}N_2O_8$ | 427.1141 | Negative |
| [4'-HPPH—H]⁻ | $C_{15}H_{11}N_2O_3$ | 269.0770 | Negative |
| [4'-HPPH—O-Glu-H]⁻ | $C_{21}H_{19}N_2O_9$ | 443.1091 | Negative |
| [Dihydrodiol-H]⁻ | $C_{15}H_{13}N_2O_4$ | 285.0875 | Negative |

Four kinds of metabolic products as well as the raw material phenytoin were separated and detected by LC. In addition, chemical constructs of the metabolic products were estimated from the location of the separated peaks in the mass spectrometry results obtained by MS/MS measurement.

The finally deduced metabolic reaction mechanism of phenytoin is shown below.

Thus, the liver-like three-dimensional construct of the present invention can be used to predict metabolic reactions that occur in a human liver using an in vitro assessment system.

Experimental Example 8 Chemical Construct Analysis of Metabolic Product of Torcetrapib A DMSO solution of Torcetrapib was prepared. The obtained drug-containing DMSO solution was added to the culture medium of the human liver-like three-dimensional construct A' fabricated in Experimental example 3' such that the concentration of the drug in the medium was 10 µmol/l. The medium was sampled up to 6 days following the drug addition, and the metabolic products in the medium were subjected to separation and structural analysis by a LC/MS/MS method. Mass chromatograms of the respective metabolic products are shown in FIG. 10. Mass numbers used for identification of the detected peaks are shown in the following table.

TABLE 5

| Compound | Molecular formula | Accurate mass number | Ion Mode |
|---|---|---|---|
| [M + HCOO]⁻ | $C_{27}H_{26}F_9N_2O_6$ | 645.1647 | Negative |
| Bistrifluoromethyl benzoic acid (M2) | $C_9H_3F_6O_2$ | 257.0037 | Negative |

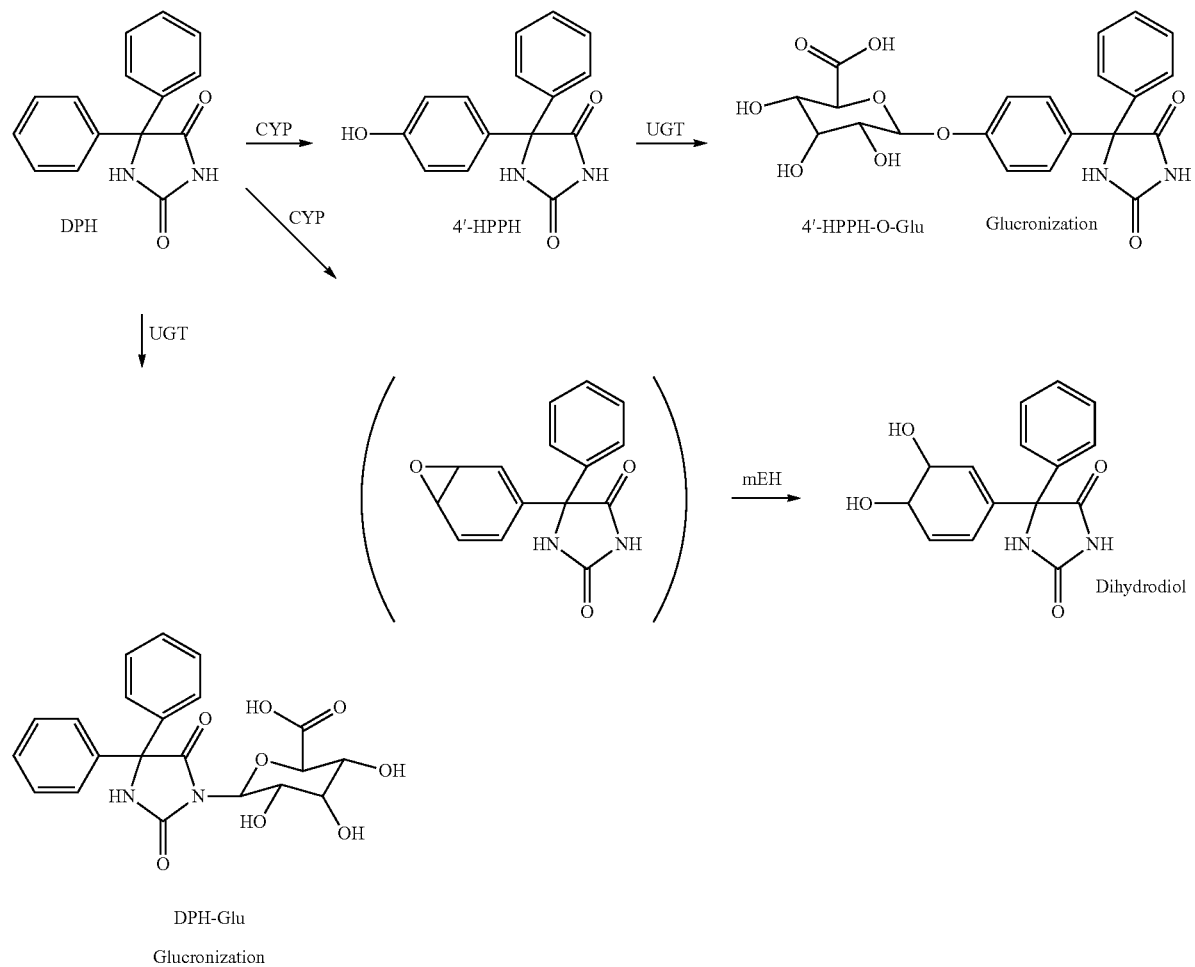

TABLE 5-continued

| Compound | Molecular formula | Accurate mass number | Ion Mode |
|---|---|---|---|
| 7-Trifluoromethyl quinaldic acid (M5) | $C_{11}H_5F_3NO_2$ | 240.0272 | Negative |

Two kinds of metabolic products M2 and M5 as well as the raw material Torcetrapib were separated and detected by LC. In addition, chemical constructs of the metabolic products were estimated from the location of the separated peaks in the mass spectrometry results obtained by MS/MS measurement. The finally deduced metabolic reaction mechanism of Torcetrapib is shown below (Drug Metab Dispos. 2008 October; 36 (10):2064-79.)

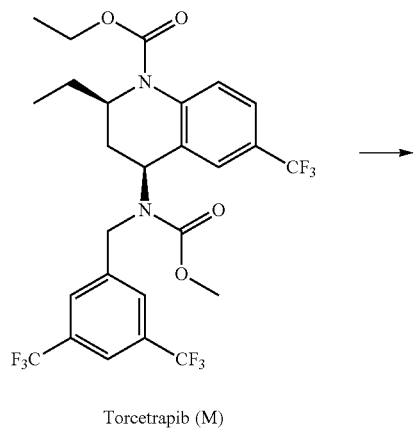

Torcetrapib (M)

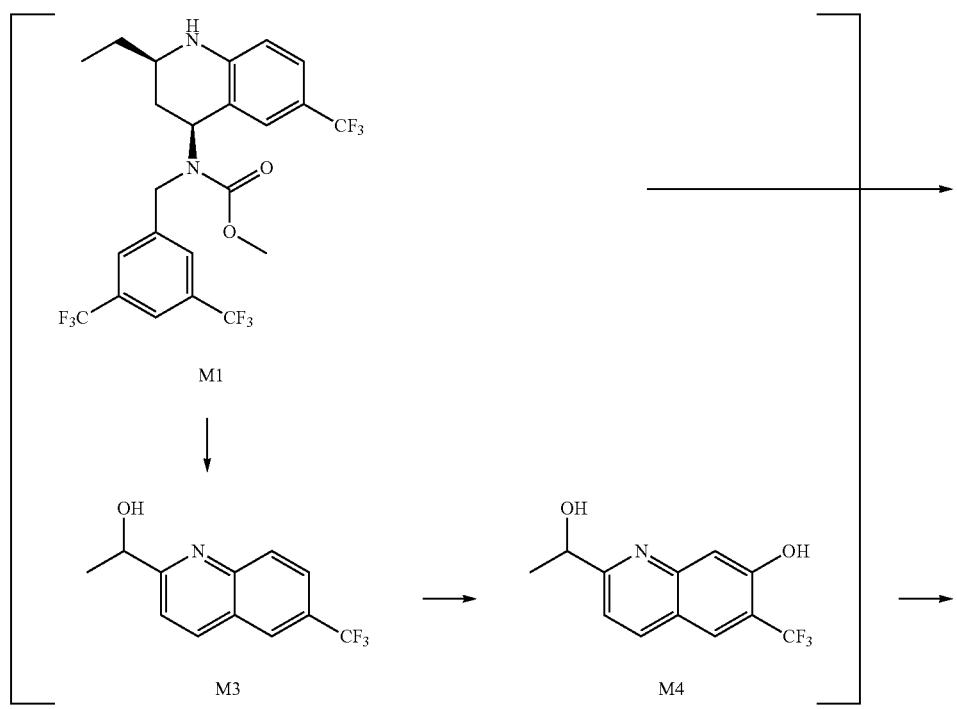

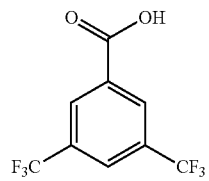

Bistrifluoromethyl benzoic acid (M2)

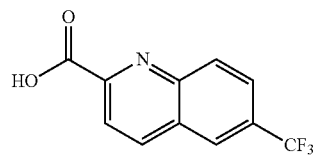

7-Trifluoromethyl quinaldic acid (M5)

Metabolic products M2 and M5 are detected when Torcetrapib (M) is administered to a human (Drug Metab Dispos. 2010 October; 38 (10):1900-5.) Thus, the liver-like three-dimensional construct of the present invention can be used to predict metabolic reactions that occur in a human liver using an in vitro assessment system.

The invention claimed is:

1. A human liver-like three-dimensional construct comprising a heterospheroid formed of an aggregate of human hepatocytes and human-derived cells other than the human hepatocytes,
wherein the other human-derived cells comprise human hepatic stellate cells;
the ratio of the number of the other human-derived cells to the number of the human hepatocytes is 0.01 or higher but lower than 1; and
wherein a cluster of the human hepatic stellate cells has a maximum projected area (equivalent circular) diameter of 100 μm.

2. The human liver-like three-dimensional construct according to claim 1, wherein the heterospheroids are stacked or blended.

3. The human liver-like three-dimensional construct according to claim 1, wherein the human hepatocytes and the other human-derived cells are homogeneously distributed.

4. The human liver-like three-dimensional construct according to claim 3, wherein the other human-derived cells comprise human hepatic stellate cells.

5. The human liver-like three-dimensional construct according to claim 1, wherein the heterospheroid is substantially spherical and has a projected area (equivalent circular) diameter of at least 1.0 mm.

6. The human liver-like three-dimensional construct according to claim 5, wherein the heterospheroid is substantially spherical and has a projected area (equivalent circular) diameter of 1.1-10.0 mm.

7. The human liver-like three-dimensional construct according to claim 6, wherein the heterospheriod is substantially spherical and has a projected area (equivalent circular) diameter of 1.2-5.0 mm.

8. The human liver-like three-dimensional construct according to claim 1, wherein the heterospheriod has a hollow or solid substantially round or substantially polygonal cylindrical shape, where an average diameter of the cross sections thereof is 1.0-10.0 mm.

9. The human liver-like three-dimensional construct according to claim 1, which has a ring shape, where an average length of the minor axes at the bottom and at the top is 1.0-10.0 mm.

10. The human liver-like three-dimensional construct according to claim 1, which has a sheet shape with an average thickness of at least 300 μm.

11. The human liver-like three-dimensional construct according to claim 10, which has a sheet shape with an average thickness of at least 500 μm.

12. A method for assessing hepatotoxicity of a test substance to a human, the method comprising:
(1) a contact step in which the test substance is brought into contact with the human liver-like three-dimensional construct according to claim 1; and
(2) a determination step in which presence or a degree of damage to the human liver-like three-dimensional construct is determined.

13. The method according to claim 12, wherein the determination step comprises an exosome collection step in which exosomes released from the three-dimensional construct are collected, and a miRNA analysis step in which a miRNA contained in the exosomes is analyzed.

14. The hepatotoxicity assessment method according to claim 12, wherein the miRNA analysis step is carried out by a microarray or PCR technique.

15. A human liver-like complex obtained by connecting two or more of the human liver-like three-dimensional constructs according to claim 1.

16. The human liver-like three-dimensional construct according to claim 1, which is obtained by fusing two or more of the heterospheroids.

17. The human liver-like three-dimensional construct according to claim 4, wherein the other human cells comprise human hepatic stellate cells, and said human hepatic stellate cells are in a quiescent state.

18. A method for assessing hepatotoxicity of a test substance to a human, comprising:
   (1) a contact step in which the test substance is brought into contact with the human liver-like three-dimensional construct according to claim 17; and
   (2) a determination step in which presence or a degree of damage to the human liver-like three-dimensional construct is determined.

19. A method for producing a human liver-like three-dimensional construct according to claim 1, comprising the steps of:
   mixing human hepatocytes and human-derived cells other than the human hepatocytes human hepatic stellate cells such that the ratio of the number of to the number of the human hepatocytes is 0.01 or higher but lower than 1, and culturing the mixture to obtain a heterospheroid formed of an aggregate of the human hepatocytes and the human-derived cells; and
   blending or stacking the heterospheroids,
   wherein the other human-derived cells comprise human hepatic stellate cells, wherein a cluster of the human hepatic stellate cells has a maximum projected area (equivalent circular) diameter of 100 μm.

20. A human liver-like three-dimensional construct obtained by the production method according to claim 19.

* * * * *